United States Patent
Rassool et al.

(10) Patent No.: US 10,105,382 B2
(45) Date of Patent: Oct. 23, 2018

(54) THERAPY REGIMEN AND METHODS TO SENSITIZE CANCER CELLS TREATED WITH EPIGENETIC THERAPY TO PARP INHIBITORS IN OVARIAN CANCER

(71) Applicants: THE JOHNS HOPKINS UNIVERSITY, Baltimore, MD (US); UNIVERSITY OF MARYLAND, BALTIMORE, Baltimore, MD (US)

(72) Inventors: Feyruz Rassool, Baltimore, MD (US); Stephen Baylin, Baltimore, MD (US); Carine Robert, Paris (FR); Khadiza Chowdhury, San Jose, CA (US); Nidal Muvarak, Baltimore, MD (US)

(73) Assignees: UNIVERSITY OF MARYLAND, BALTIMORE, Baltimore, MD (US); THE JOHNS HOPKINS UNIVERSITY, Baltimore, MD (US)

( * ) Notice: Subject to any disclaimer, the term of this patent is extended or adjusted under 35 U.S.C. 154(b) by 221 days.

(21) Appl. No.: 15/254,716

(22) Filed: Sep. 1, 2016

(65) Prior Publication Data
US 2016/0367581 A1 Dec. 22, 2016

Related U.S. Application Data

(63) Continuation of application No. 15/112,768, filed as application No. PCT/US2015/012244 on Jan. 21, 2015.

(60) Provisional application No. 61/929,680, filed on Jan. 21, 2014.

(51) Int. Cl.
| | | |
|---|---|---|
| *A61K 31/706* | (2006.01) | |
| *A61K 31/4184* | (2006.01) | |
| *A61K 31/7068* | (2006.01) | |
| *A61K 31/145* | (2006.01) | |
| *A61K 31/166* | (2006.01) | |
| *A61K 31/496* | (2006.01) | |
| *A61K 31/502* | (2006.01) | |
| *A61K 31/55* | (2006.01) | |
| *A61K 31/5025* | (2006.01) | |

(52) U.S. Cl.
CPC .......... *A61K 31/706* (2013.01); *A61K 31/145* (2013.01); *A61K 31/166* (2013.01); *A61K 31/4184* (2013.01); *A61K 31/496* (2013.01); *A61K 31/502* (2013.01); *A61K 31/5025* (2013.01); *A61K 31/55* (2013.01); *A61K 31/7068* (2013.01)

(58) Field of Classification Search
CPC ... A61K 31/706; A61K 31/145; A61K 31/166
See application file for complete search history.

(56) References Cited

FOREIGN PATENT DOCUMENTS

| | | |
|---|---|---|
| WO | 2011/130689 | 10/2011 |
| WO | 2012/178125 | 12/2012 |
| WO | 2016/142427 | 9/2016 |

OTHER PUBLICATIONS

Caiafa; Journal of Cellular Physiology, 2009, 219, 265-270.*
Extended European Search Report dated Dec. 20, 2017 in corresponding European Application No. 15740207.4.
Mani et al., "DNA Demethylating Agents and Epigenetic Therapy of Cancer", Advances in Genetics, 70:327-340 (2010).
Orta et al., "The PARP inhibitor Olaparib disrupts base excision repair of 5-aza-2'-deoxycytidine lesions", Nucleic Acids Research, 42(14):9108-9120 (2014).
Pulliam et al., "Novel combination therapy of DNMT inhibitor SGI-110 and PARP inhibitor BMN-673 (talazoparib) for BRCA-proficient ovarian cancer", Cancer Research, 75(suppl.15):2943 (2015).
Muvarak et al., "Enhancing the Cytotoxic Effects of PARP Inhibitors with DNA Demethylating Agents—A Potential Therapy for Cancer", Cancer Cell, 30(4):637-650 (2016).
Baylin SB et al.: "A decade of exploring the cancer epigenome—biological and translational implications", Nat Rev Cancer, vol. 11(10): pp. 726-734, (2011).
Blum W et al.: "Phase I study of decitabine alone or in combination with valproic acid in acute myeloid leukemia", Journal of Clinical Oncology, vol. 25: pp. 3884-3891, (2007).
Bryant H E et al.: "Specific killing of BRCA2-deficient tumours with inhibitors of poly(ADP-ribose) polymerase", Nature Publishing Group, vol. 434: pp. 913-917, (2005).
Caiafa P et al.: "Epigenetics: poly(ADP-ribosyl) ation of PARP-1 regulates genomic methylation patterns" FASEB Journal vol. 23, 672-678, (2016).
Gaymes TJ et al.: "Inhibitors of poly ADP-ribose polymerase (PARP) induce apoptosis of myeloid leukemic cells: potential for therapy of myeloid leukemia and myelodysplastic syndromes", Haematologica., vol. 94(5): pp. 638-646, (2009).
Helleday T et al: "Poly(ADP-ribose) polymerase (PARP-1) in homologous recombination and as a target for cancer therapy",Cell Cycle, 4(9):pp. 1176-1178, (2005).
Helleday T et al: "DNA repair pathways as targets for cancer therapy", Nat Reviews Cancer, vol. 8, pp. 193-204, (2008).
Isakoff SJ et al.: "Triple-negative breast cancer: role of specific chemotherapy agents", Cancer J vol. 16(1), pp. 53-61, (2010).
Kantarjian H et al.: "Decitabine improves patient outcomes in myelodysplastic syndromes", Results of a phase III randomized study, American Cancer Society, vol. 106, pp. 1794-1803, (2006).
McCabe N et al.: "Deficiency in the repair of DNA Damage by Homologous Recombination and Sensitivity to Poly (ADP-Ribose) Polymerase Inhibition", Cancer Res. 2006, 66(16): pp. 8109-8115.
Murai J et al.:"Differential Trapping of PARP1 and PARP2 by Clinical PARP Inhibitors", Cancer Res 72(21) 5588-5599. (2012).

(Continued)

*Primary Examiner* — Pancham Bakshi
(74) *Attorney, Agent, or Firm* — Wenderoth, Lind & Ponack, L.L.P.

(57) ABSTRACT

The presently disclosed subject matter provides methods to treat cancer cells using low doses of DNA demethylating agents and poly ADP ribose polymerase (PARP) inhibitors. Methods also are provided for sensitizing a cell to a PARP inhibitor.

15 Claims, 22 Drawing Sheets

Specification includes a Sequence Listing.

(56) References Cited

OTHER PUBLICATIONS

Rassool FV et al.: "Targeting abnonnal DNA double strand break repair in cancer" Cell Mol Life Science, 67(21): pp. 3699-3710, (2010).
Robert C et al.: "HDAC inhibitors: Roles of DNA Damage and Repair", Advances in Cancer Research vol. 16 pp. 87-129, (2012).
Rouleau M et al.: "PARP inhibition: PARP1 and beyond", Nat Rev Cancer, 10(4): pp. 293-301, (2010).
Sallmyr A et al.: "Internal tandem duplication ofFLT3 (FLT3/ITD) induces increased ROS production, DNA damage, and misrepair: implications for poor prognosis in AM" Blood, vol. 111, pp. 3173-3182 (2008).
Sallmyr A et al.: "Up-regulation of WRN and DNA ligase III$\alpha$ in chronic myeloid leukemia: consequences for the repair ofDNA double-strand breaks" Blood 112(4), pp. 1413-1423, (2008).
Shen Yet al.: "BMN 673, a Novel and Highly Potent PARP1/2 Inhibitor for the Treatment of Human Cancers with DNA Repair Deficiency" Clinical Cancer Research, 19, pp. 5003-5015, (2013).
Tobin LA et al. "Targeting abnormal DNA repair in therapy-resistant breast cancers", Mol Cancer Research, 10(1): pp. 96-107, (2012).
Tobin LA et al. "Targeting abnormal DNA double-strand break repair in tyrosine kinase inhibitor-resistant chronic myeloid leukemias", Oncogene, 32(14), pp. 1784-1793, (2013).
Tsai HC et al. "Transient low doses of DNA Demethylating Agents Exert Durable Anti-tumor Effects on Hematological and Epithelial Tumor Cells", Cancer Cell, 21(3): pp. 430-446, (2012).

\* cited by examiner

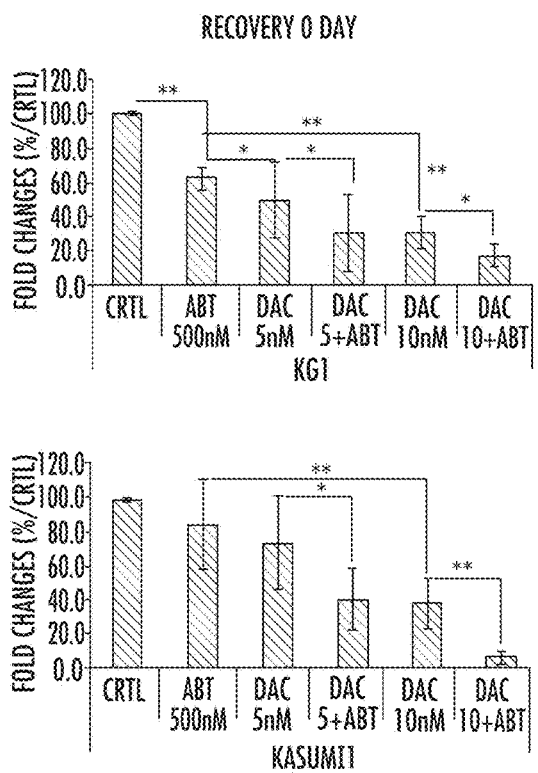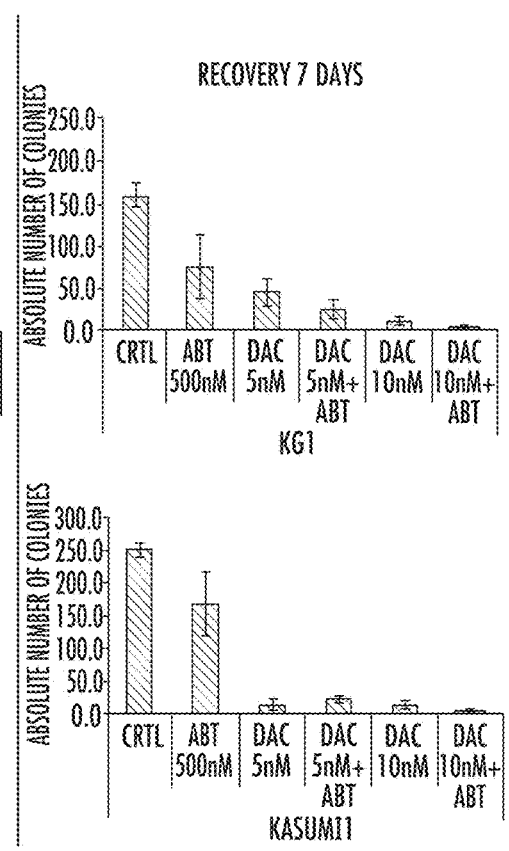
FIG. 4A
FIG. 4B

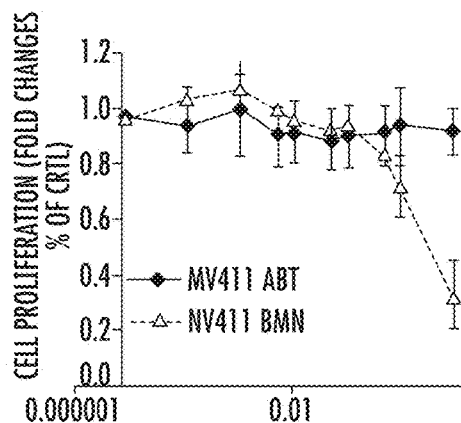
FIG. 5A
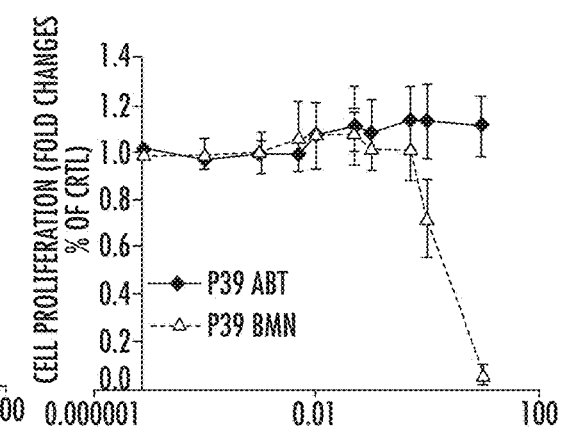
FIG. 5B
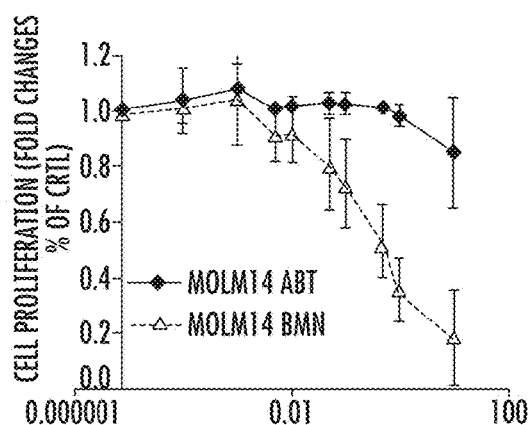
FIG. 5C
| SAMPLES | MV411 ABT | MV411 BMN | MOLM14 ABT | MOLM14 BMN | P39 ABT | P39 BMN |
|---|---|---|---|---|---|---|
| IC50 (μM) | 475 | 6.45 | 27.27 | 4.46 | 0 | 4.87 |
FIG. 5D

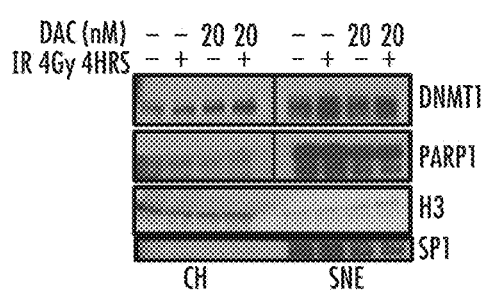
FIG. 15A
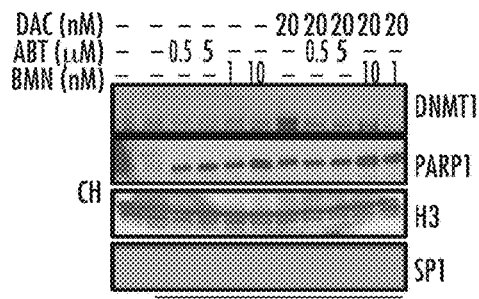
FIG. 15B
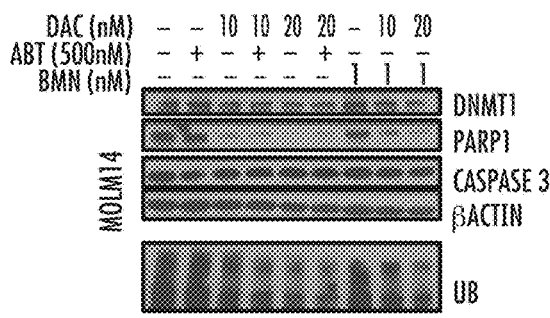
FIG. 15C
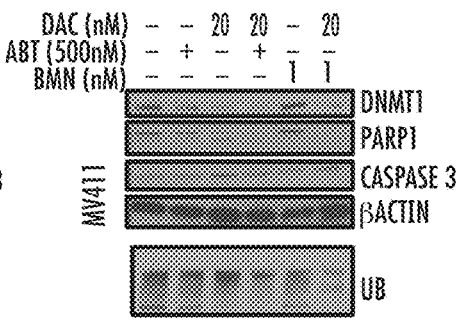
FIG. 15D
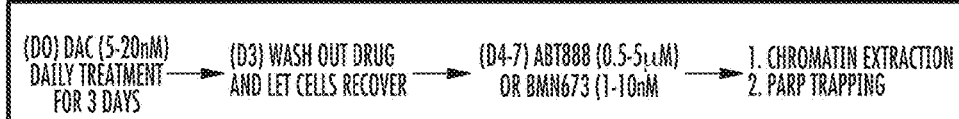
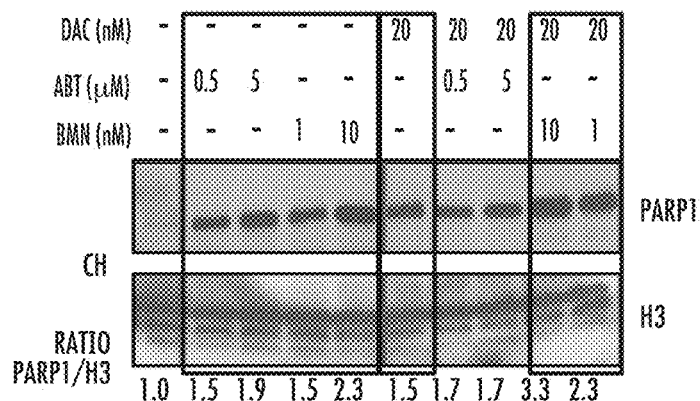
FIG. 15E

FIG. 21A

| PT# | SPECIMEN | SEX | BM blasts @Dx | PB blasts @Dx | CYTOGENETICS | FLT-3 MUTATION | NPM-1 MUTATION | RESPONSE TO DAC/AzaC +ABT/BMN* |
|---|---|---|---|---|---|---|---|---|
| 9 | BM | F | - | - | 49,XX,-11,+21,+3mar[11]/49,XX,i(11)(q10),+3mar[3]/46,XX[5] | - | - | NO |
| 15 | BM | M | - | - | | - | - | YES |
| 16 | BM | F | 35 | 21 | 46,XX | ITD | - | NO |
| 18 | PB | F | - | - | 46,XX,t(1;5)(q25;q13)[5]/46,XX[15] w/84% ALLELIC BURDEN | ITD | TBD | TBD |
| 29 | PB | F | - | 95 | 46,XX | ITD | WT | YES |
| 30 | BM | F | - | 5 | 46,XX | WT | MUT | NO |
| 34 | PB | F | | | TBD | ITD | TBD | YES |
| 81 | BM | | | | TBD | | | YES |
| 86 | BM | M | N/A | TBD | TBD | TBD | TBD | YES |
| 90 | PB | | | | TBD | TBD | TBD | YES |
| 92 | BM | | /8 | | TBD | TBD | TBD | YES |

FIG. 21B

| CELL LINE | SUBTYPE | TRANSLOCATIONS | KARYOTYPE | FLT-3 MUTATION | NPM-1 MUTATION | TREATMENT | SENSITIVITY TO DAC/ABT COMBINATION* | SENSITIVITY TO DAC/BMN COMBINATION* |
|---|---|---|---|---|---|---|---|---|
| KASUMI | M2 | (AML1-ETO) | t(8;21)(q22;q22) | NO | NO | DAC/ABT | YES | TBD |
| MOLM14 | M5 | MLL-AF9 | 49,XY,+6,+8 INS(11;9)(q23;p22p23),+13 | ITD (+/-) | NO | DAC/ABT AND DAC/BMN | YES | YES |
| MV4-11 | M4 | MLL-AF4 | 48,XY,t(4;11)(qw21;q23),+8,+19 | ITD (+/+) | NO | DAC/ABT AND DAC/BMN | YES | YES |

THERAPY REGIMEN AND METHODS TO SENSITIZE CANCER CELLS TREATED WITH EPIGENETIC THERAPY TO PARP INHIBITORS IN OVARIAN CANCER

CROSS-REFERENCE TO RELATED APPLICATIONS

This application claims the benefit of U.S. Provisional Application No. 61/929,680, filed Jan. 21, 2014, which is incorporated herein by reference in its entirety.

INCORPORATION-BY-REFERENCE OF MATERIAL SUBMITTED ELECTRONICALLY

This application contains a sequence listing. It has been submitted electronically via EFS-Web as an ASCII text file entitled "111232-00370_ST25.txt". The sequence listing is 710 bytes in size, and was created on Jan. 21, 2015. It is hereby incorporated by reference in its entirety.

BACKGROUND

Acute myeloid leukemias (AML) are a heterogeneous disease sub-divided into cytogenetics and molecular subsets characterized by favorable and unfavorable response to current therapies. Fms-like tyrosine kinase 3 internal tandem duplication (FLT3/ITD) is a constitutively active tyrosine kinase expressed in 30% of all AMLs cases. FLT3/ITD-expressing cells are considered one of most "unfavorable subsets" of AML with no effective treatment, suggesting the urgent need for the development of new therapies.

Several lines of evidence suggest that genomic instability in myeloid malignancies is promoted by increased endogenous DNA damage and error-prone repair that lead to disease progression and resistance to therapy. Poly-(ADP)-ribose polymerase (PARP) participates in single strand break (SSB) repair, as well as highly error-prone pathway repair for double strand breaks (DSBs). Leukemia cells are sensitive to PARP inhibitors, such as ABT888 (Veliparib; Abbott Laboratories, North Chicago, Ill.), suggesting their dependence on PARP activity for survival. BMN673 (BioMarin Pharmaceuticals, San Rafael, Calif.) is a novel and highly potent PARP1/2 inhibitor that has been tested in clinical trials against solid tumors carrying a DSB repair deficiency, such as a BRCA1 mutation. Recently, it has been demonstrated that in addition to catalytic inhibition of PARP, PARP inhibitors induce cytotoxic PARP-DNA complexes that could be held responsible for their therapeutic effect. Such a mechanism has been reported for the PARP inhibitor BMN673 (Murai et al., 2014).

Recent studies have demonstrated that leukemia cell lines and primary cells that are resistant to tyrosine kinase inhibitors and therapy-resistant derivatives of ER/PR+ and ER/PR− breast cancer cells, including primary tissue biopsies for the latter, have increased activity of a highly error-prone and alternative DSB repair pathway termed alternative non homologous end-joining (ALT NHEJ). These cells also upregulate the steady state levels of PARP1 and DNA ligase IIIα, components involved in this pathway. These cells, as well as leukemia cells resistant to tyrosine kinase inhibitors, have increased sensitivity to the combination of PARP and DNA ligase IIIα inhibitors as demonstrated by an increased number of DSBs and significantly increased colonies in colony survival assays (Tobin et al., 2012; Tobin et al., 2013). These results suggest ALT NHEJ is a novel therapeutic target, closely dependent on PARP1, in breast cancers and leukemias which are dependent upon this mode of DNA repair for survival.

SUMMARY

In one aspect, the presently disclosed subject matter provides a method for treating a cancer, the method comprising administering to a subject in need of treatment thereof an effective amount of a low dose of a DNA demethylating agent and an effective amount of a poly ADP ribose polymerase (PARP) inhibitor. In particular aspects, the DNA demethylating agent is a DNA methyltransferase inhibitor (DNMTi). In certain aspects, the cancer is selected from the group consisting of leukemia, such as acute myeloid leukemia (AML), myelodysplastic syndrome (MDS), breast cancers, and ovarian cancers.

In other aspects, the presently disclosed subject matter provides a method for sensitizing a cell to a poly ADP ribose polymerase (PARP) inhibitor, the method comprising contacting the cell with an effective amount of a low dose of a DNA demethylating agent prior to contacting the cell with an effective amount of the PARP inhibitor.

In some aspects, the presently disclosed subject matter provides a method for reducing repair of double-strand breaks in DNA in a cell, the method comprising contacting the cell with an effective amount of a low dose of a DNA demethylating agent and with an effective amount of a poly ADP ribose polymerase (PARP) inhibitor.

In certain aspects, the presently disclosed subject matter provides a method for increasing cytotoxic DNA-poly ADP ribose polymerase (PARP) complexes in a cell, the method comprising contacting the cell with an effective amount of a low dose of a DNA demethylating agent and with an effective amount of a PARP inhibitor.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
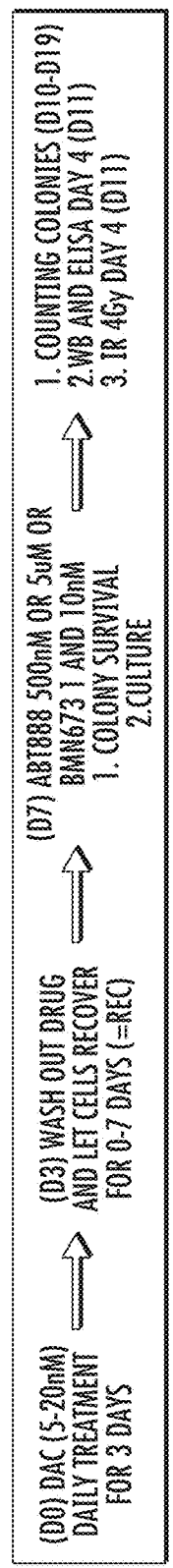
Figure 6A:
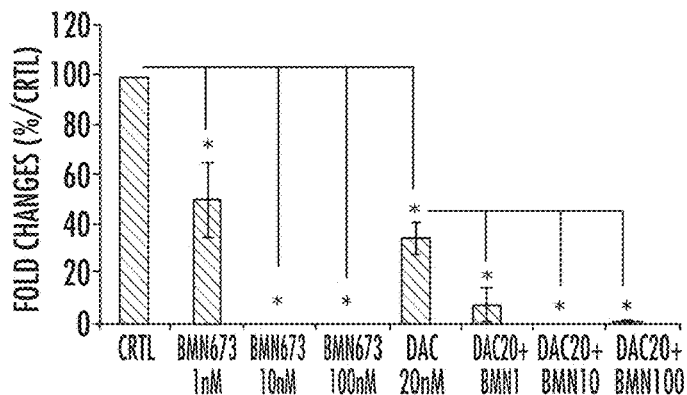
Figure 6B:
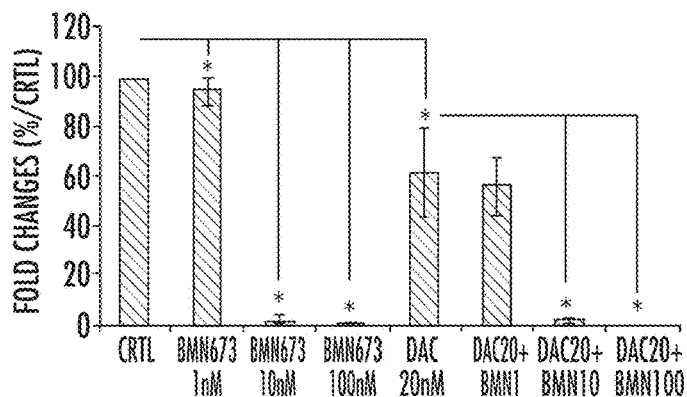
Figure 6C:
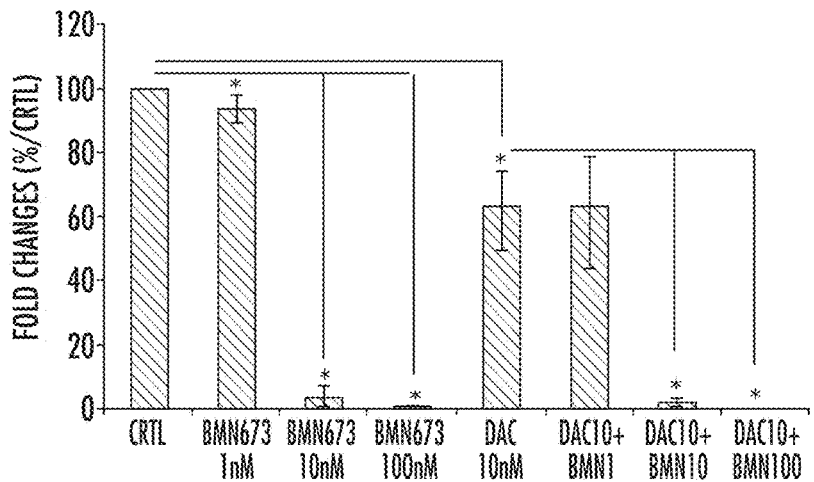
Figure 7A:
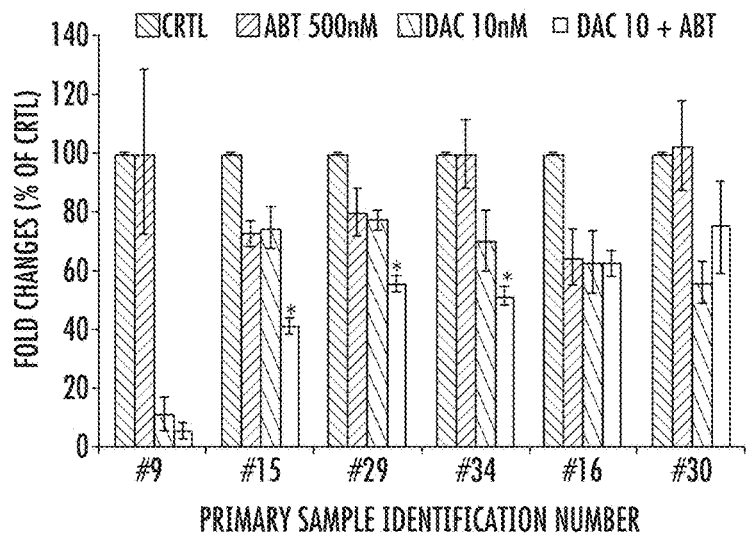
Figure 7B:
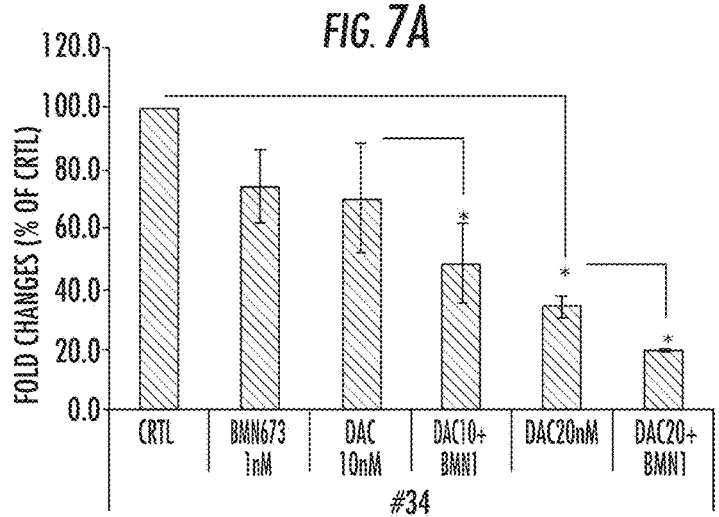
Figure 7C:
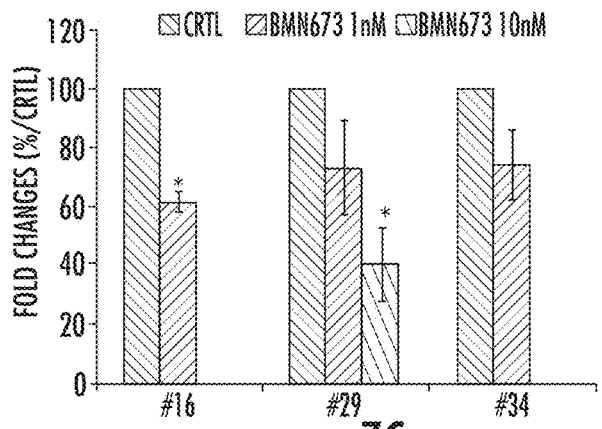
Figure 8A:
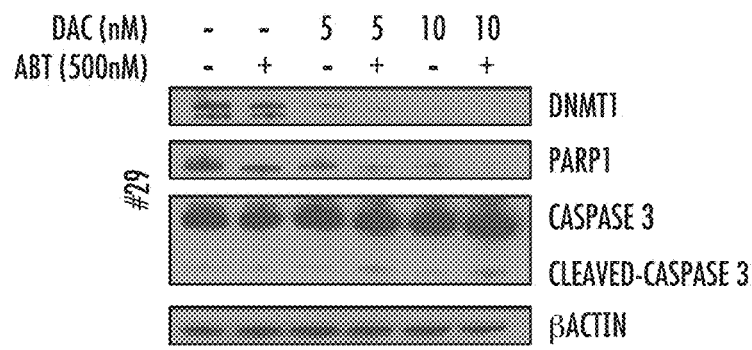
Figure 8B:
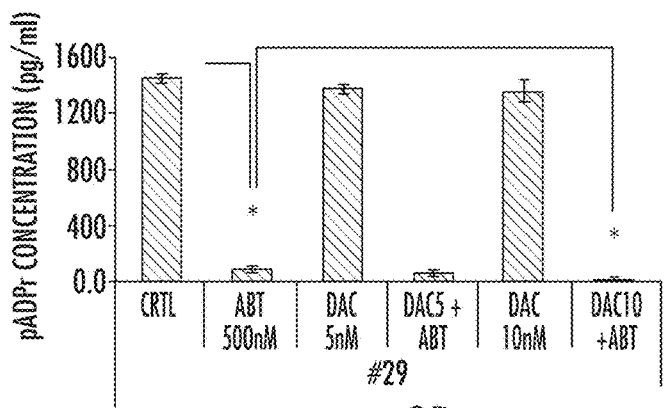
Figure 8C:
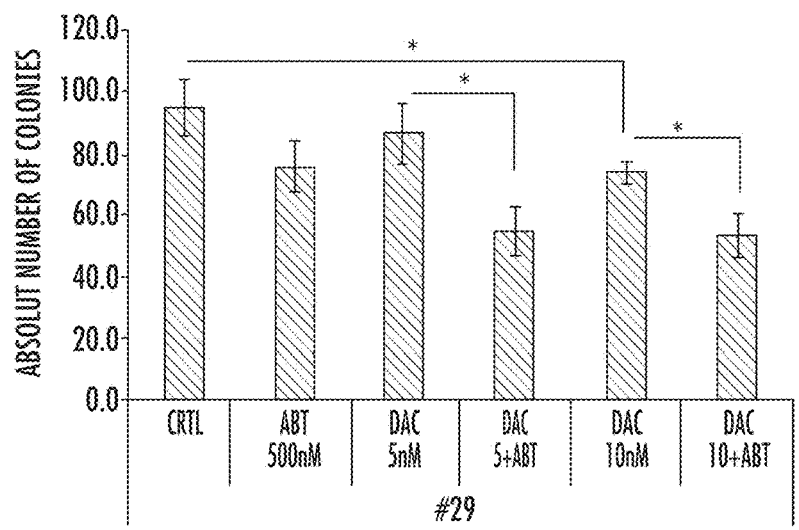
Figure 9A:
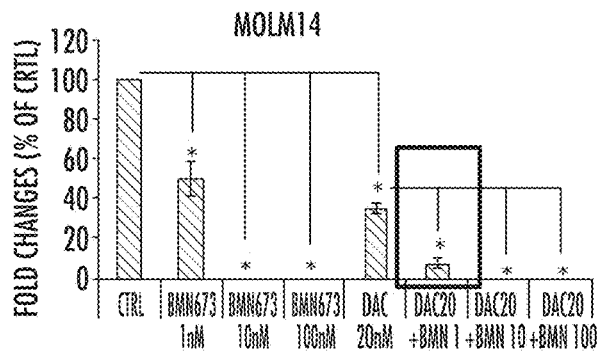
Figure 9B:
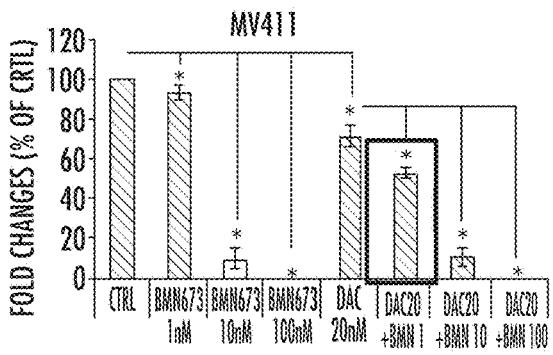
Figure 9C:
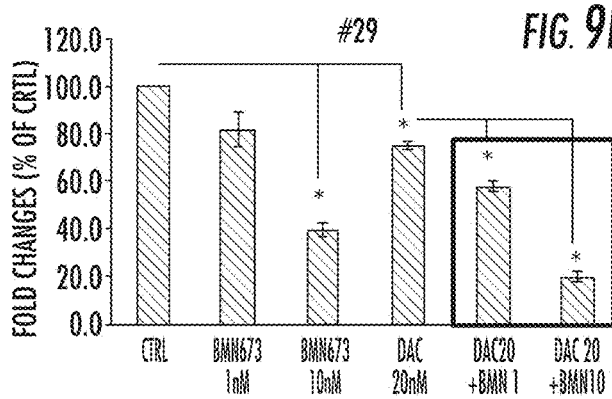
Figure 9D:
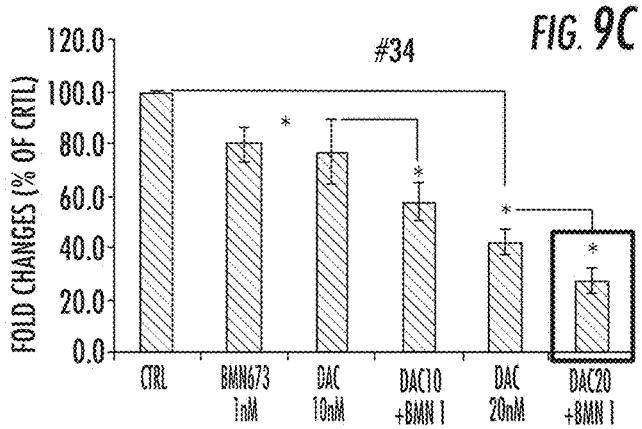
Figure 10A:
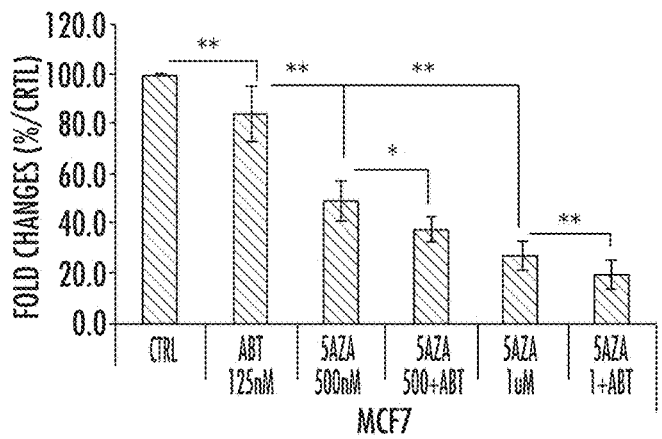
Figure 10B:
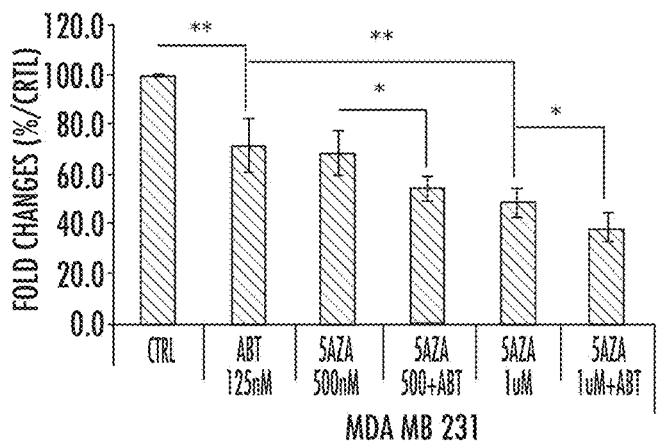
Figure 10C:
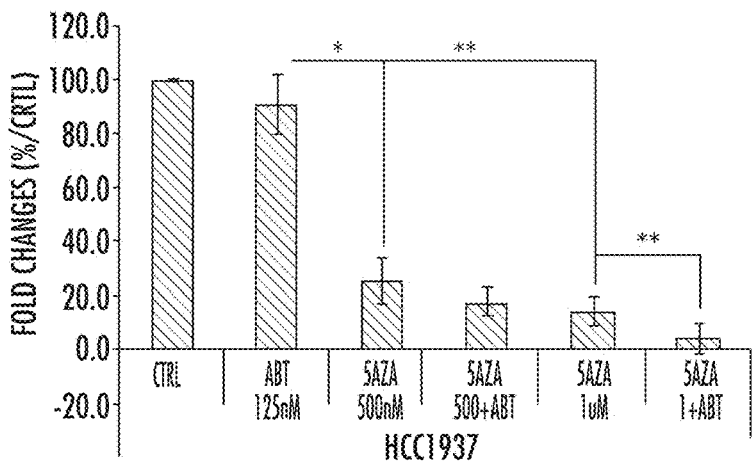
Figure 11A:
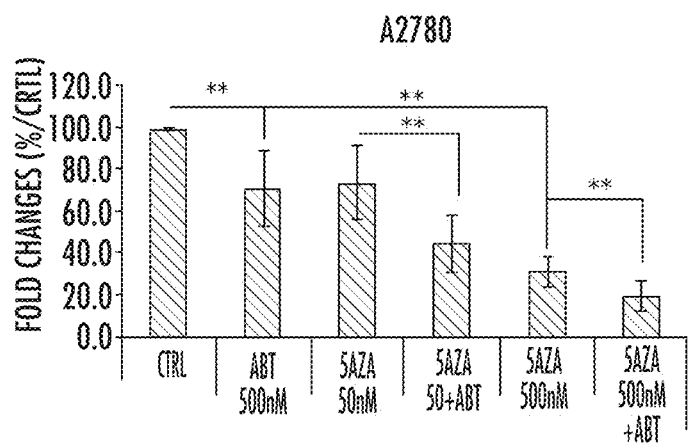
Figure 11B:
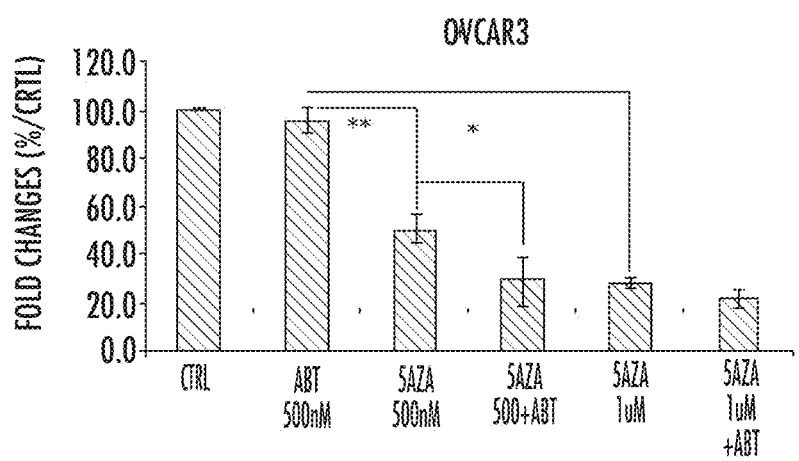
Figure 12A:
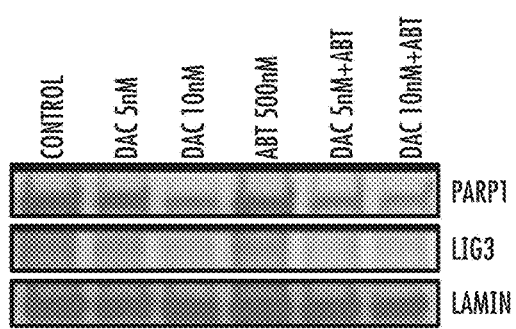
Figure 12B:
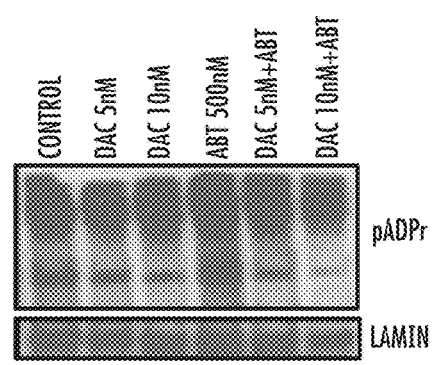
Figure 13:
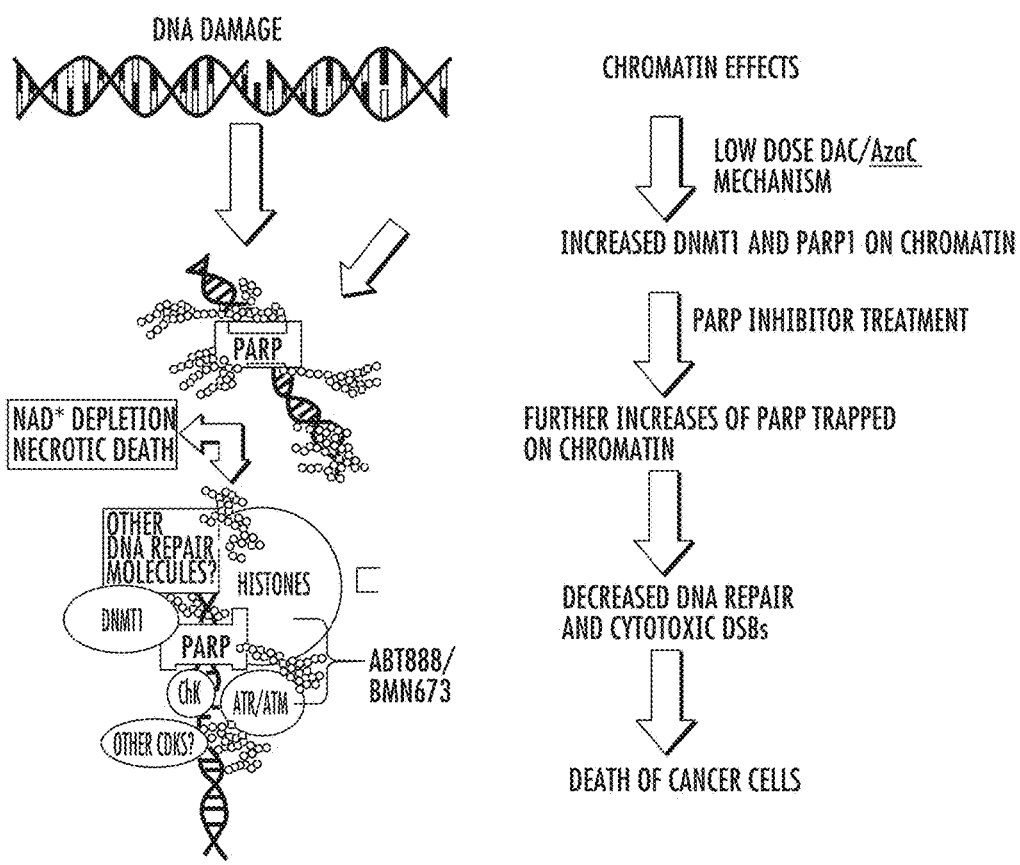
Figures 14A, 14B:
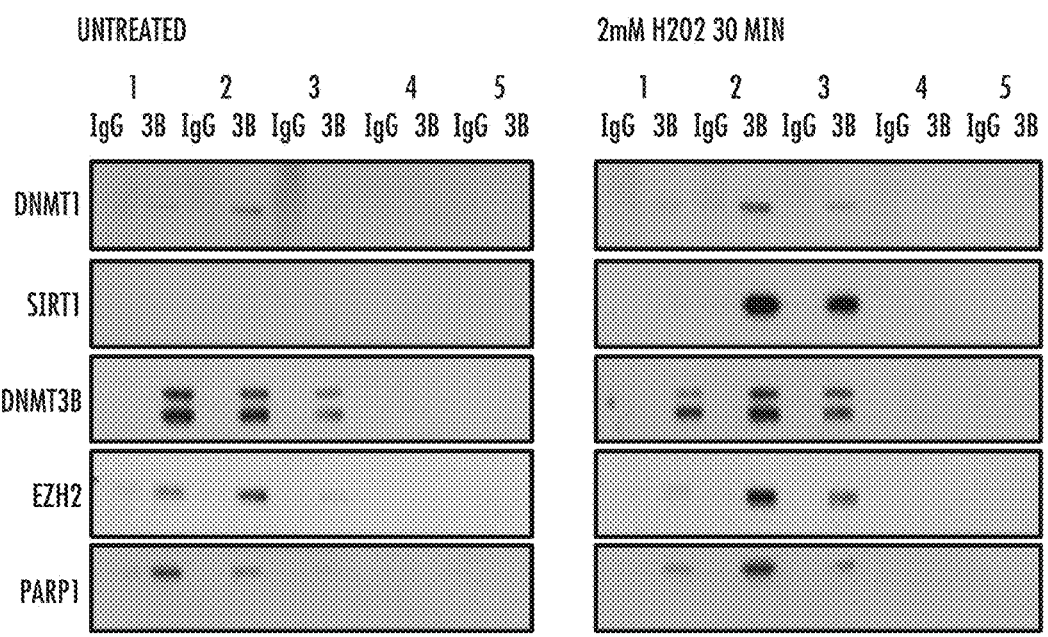
Figure 18:
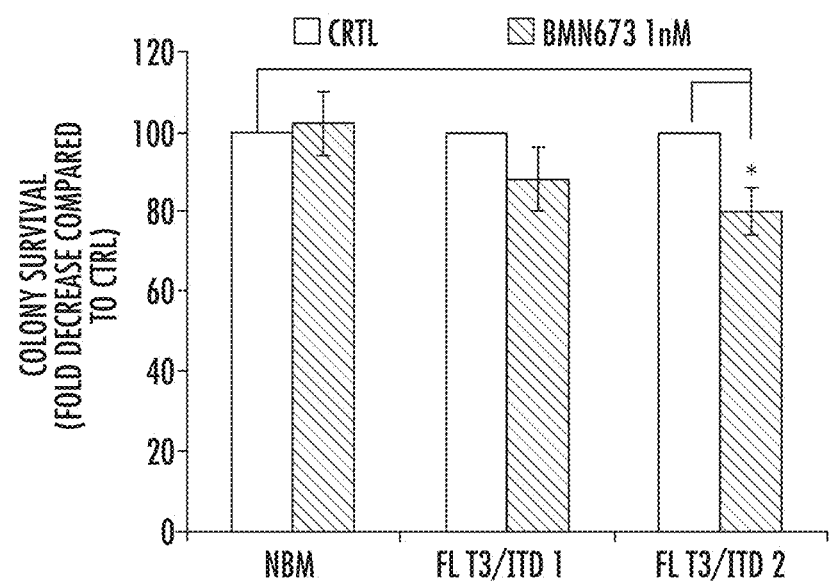
Figure 20:
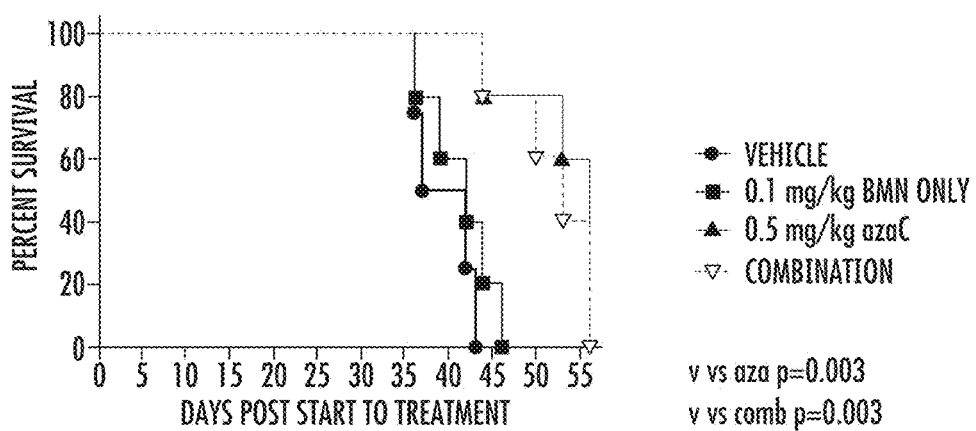
Figure 22B:
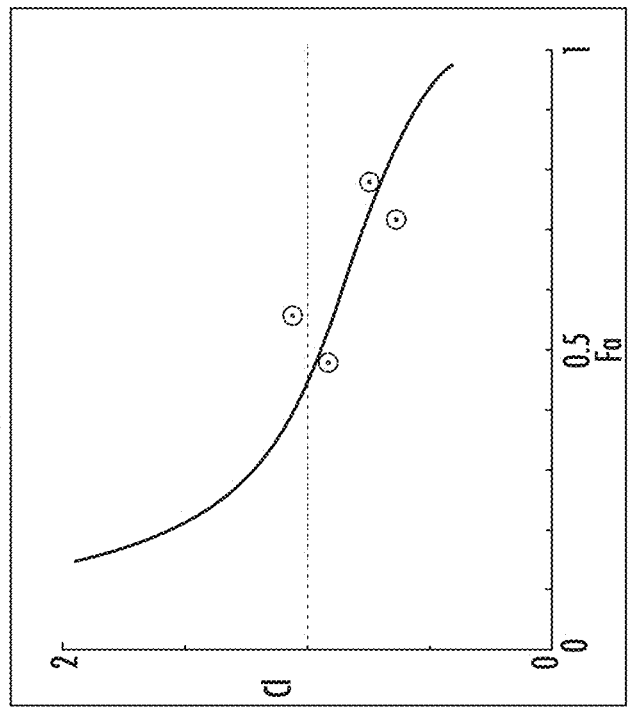
Figure 22A:
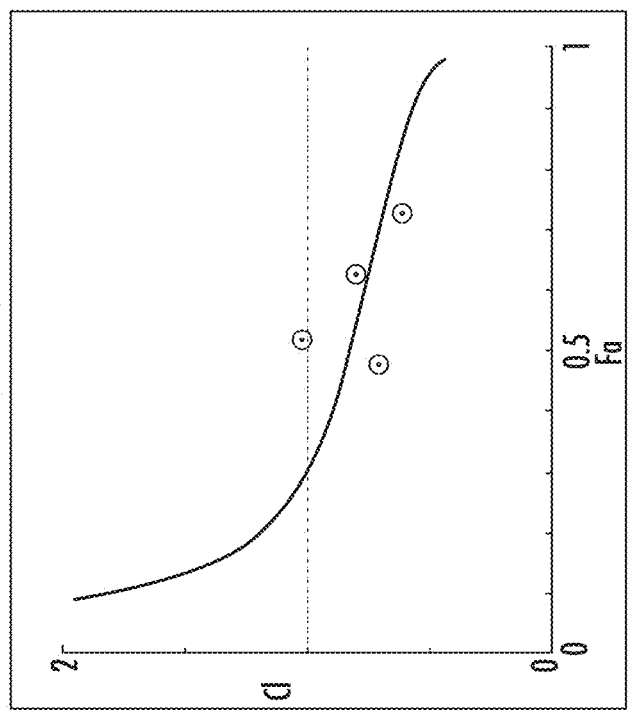

Having thus described the presently disclosed subject matter in general terms, reference will now be made to the accompanying Figures, which are not necessarily drawn to scale, and wherein:

FIG. 1 shows a schematic diagram of an embodiment of drug treatment and timeline of a presently disclosed protocol;

FIGS. 2A-2D show a methylcellulose clonogenic assay of: (A) Kasumi-1 (AML1-ETO); (B) MOLM14 REC D4 (FLT3-ITD−/+); (C) MV411 (FLT3-ITD+/+); and (D) MOLM14 REC D7 after treatments and recovery period (REC) as described in FIG. 1. Results are representative of at least 2 experiments in triplicate +/−SEM. *p<0.05 by T-test compared to CRTL if not indicated otherwise;

FIGS. 3A-3G show: (A)-(D) ELISA assays measuring total level of poly-(ADP)-ribose in KASUMI1 (A), KG1 (B), MOLM14 (C) and MV411 (D) cells after treatments and recovery period of 7 days. Results are representative of 3 experiments in triplicate +/−SEM. *p<0.05 by T-test compared to CRTL if not indicated otherwise; and (E)-(G) Colony survival assays performed as described (Tsai et al., 2012) and colonies were counted 21 days after ABT treatment in KASUMI-1 (E) and KG1 (F) cells and 10 days after ABT treatment in MOLM14 (G) cells. (E and F) Fold changes of 3 experiments in triplicated are represented, ±80 p<0.05 and ** p<0.01 by T-test. (G) Average number of colonies of 2 experiments in triplicate is presented, ±80;

FIGS. 4A-4B show the effect of the length of the recovery period on the clonogenicity of AML cell lines KG1 and KASUMI1: (A) No recovery period; and (B) 7 days of recovery;

FIGS. 5A-5D show an MTS assay after four days of: (A) MV411; (B) P39; (C) MOLM14 treatment with increasing doses of ABT888 or BMN673; and (D) shows the IC50 results which were measured based on three independent experiments +/−SEM;

FIGS. 6A-6C show a clonogenic assay in methylcellulose: (A) MOLM14; (B) MV411 cells pretreated for 3 days with DAC (20 nM), followed by a recovery period of 4 days and subsequent treatment with BMN673 (1 nM, 10 nM and 100 nM). Ten days later, stained colonies containing more than 40 cells were quantified; and (C) shows a methylcellulose clonogenic assay of MV411 cells pretreated for 3 days with DAC (10 nM), followed by a recovery period of 4 days. Results (fold changes compared to CRTL treatment) are representative of the mean±SEM of at least two independent experiments in triplicate. * p<0.05 by T-test compared to CRTL if not indicated otherwise;

FIGS. 7A-7C show a clonogenic assay in methylcellulose of mononuclear cells (MNC) from 6 AML patients. Cells were pretreated for 3 days with DAC (10 nM-20 nM), followed by a recovery period of 4 days and subsequent treatment with: (A) ABT888 (500 nM) using samples from patients #9, #15, #29, #34, #16 and #30 (bars in order from left to right for each sample are CRTL, ABT (500 nM), DAC (10 nM), DAC (10 nM+ABT); (B) BMN673 (1 nM) using a sample from patient #34; and (C) BMN673 using samples from patients #16, #29, and #34 (bars are CRTL on left and BMN673 1 nM on right for patients #16 and #34; and CRTL on left, BMN673 (1 nM) in middle, and BMN673 (10 nM) on right for patient #34). Ten days later, stained colonies containing more than 40 cells were quantified and results (fold changes compared to CRTL treatment) are representative of the mean±SEM of at least one experiment in triplicate. * p<0.05 by T-test;

FIGS. 8A-8C show: (A) Western blot analysis of DNA methyltransferase 1 (DNMT1), PARP1, and Caspase 3 of total extract of bone marrow mononuclear cells (BMMNC) from patient #29 treated with DAC and/or ABT (β-actin, loading control); (B) ELISA assay measuring total level of poly-(ADP)-ribose (pADP) in BMMNC from patient #29; and (C) clonogenicity is decreased by DAC and further decreased by DAC and ABT888 in bone marrow mononuclear cells obtained from patient (#29). There were 4 days of recovery between the DNMTi and PARPi treatment. Results are representative of at least 1 experiment in triplicate +/−SEM. *p<0.05 by T-test compared to CRTL if not indicated otherwise;

FIGS. 9A-9D show that AML cell lines MOLM14 (A) and MV411 (B) and primary cells from patients #29 (C) and #34 (D) are more sensitive to a combination of DAC (10 nM-20 nM) and BMN673 (1 nM);

FIGS. 10A-10C show that clonogenicity is decreased by 5AZA and further decreased by 5AZA and ABT888 using breast cancer cells: (A) MCF7; (B) MDA MB231; and (C) HCC1937. There were 7 days of recovery between the DNMTi and PARPi treatment;

FIGS. 11A-11B show that clonogenicity is decreased by 5AZA and further decreased by 5AZA and ABT888 using ovarian cancer cells: (A) A2780; and (B) OVCAR3. There were 7 days of recovery between the DNMTi and PARPi treatment;

FIGS. 12A-12B show Western blot analysis of: (A) PARP1 and LIG3; and (B) pADPr using MOLM14 cells treated with control, DAC (5 nM and 10 nM), ABT888 (500 nM), or a combination of both. Lamin is used as loading control;

FIG. 13 shows a schematic diagram of damage to a DNA molecule and how PARP1 and the epigenetic pathways interact;

FIGS. 14A-14B show that PARP1 interacts with DNMT's as evidenced by co-immunoprecipitation assays performed on sucrose gradient fractions, which define the complex size before and after damage;

FIGS. 15A-15E show: (A)-(B) Western blot analysis of DNMT1, PARP1, and Histone3 using chromatin fraction (CH) and soluble nuclear fraction (SNE) of MV411 cells subjected to (+) or not subjected to (−) 4Gy x-ray irradiation for four hours (SP1, loading control); (C)-(D) Western blot analysis of ubiquitin (UB), DNA methyltransferase 1 (DNMT1), PARP1 and Caspase 3 of total extract of MOLM14 (C) and MV411 (D) in the absence of 4Gy x-ray irradiation (β-actin, loading control); and (E) DNMTi decitabine or PARPi (ABT888 or BMN 673) treatment alone traps PARP into chromatin, but the two drugs in combination trap more PARP1 in chromatin: MV411 were treated daily for 3 days with 20 nM of DAC, allowed to recover without any drug treatment for 4 days followed by subsequent ABT888 (ABT, 5 µM), BMN673 (BMN, 10 nM) or control treatment. Four hours before the extraction of the chromatin (CH) fraction, MV411 cells were subjected to 4Gy X-Ray irradiation. Western blot analysis was then performed for DNMT1, PARP1, and H3 as a loading control;

FIGS. 16A-16D show that decitabine and subsequent treatment with PARPi's increase DNA damage and decrease NHEJ DNA repair efficiency. MV411 cells were treated with DAC (20 nM), let to recover without any drug treatment for 4 days followed by subsequent ABT888 (ABT, 5 µM), BMN673 (BMN, 10 nM) or control treatment: (A) schematic of the experiment. NHEJ DNA repair efficiency was measured after IsceI-linearized EJ2 plasmid was ligated in the presence of nuclear extract (NUC+CH) from MV411 treated with DAC (20 nM), allowed to recover without any drug treatment for 4 days followed by subsequent ABT888 (ABT, 5 µM), BMN673 (BMN, 10 nM) or control treatment and 4 hours after 4Gy X-Ray irradiation followed by overnight ligation; (B) DNA was purified and primers flanking the IsceI site of EJ5GFP were used to PCR amplify a band of Xbp that represent NHEJ DNA repair efficiency. H3 was used a loading control for the amount of nuclear extract used for ligation. Ratio of Xbp band over H3 intensities was measured and NHEJ repair efficiency is represented as fold changes compared to CRTL; (C) NHEJ repair efficiency is represented as fold changes compared to CRTL; and (D) treated cells were harvested and immunofluorescence for γH2AX was performed before (Ai) or after (Aii) 4Gy X-Ray irradiation;

FIGS. 17A-17D show the percent survival relative to the control using patient samples: (A) #081; (B) #086; (C) #090; and (D) #092 with BMN (5 nM), DAC (10 nM), DAC and BMN, AZA (100 nM) or AZA and BMN. Combination therapies were administered simultaneously rather than sequentially;

FIG. 18 shows colony survival using BMN (1 nM) with normal bone marrow (NBM) and AML cells carrying the very poor prognostic marker, FLT3/ITD mutations (FLT3/ITD1 and FLT3/ITD2) (CRLT on left and BMN on right for each sample);

FIGS. 19A-19F show that AML xenografts are sensitive to the combination of DAC and PARPi's: (A) luciferase imaging of mice in different treatment groups showing average photon counts at days 1, 16 and 30 post treatment; (B) graph of average photon counts as a percentage of control in different groups post treatment. * $p<0.01$, veh vs combination; ** $p<0.01$, aza vs combination; * $p=0.04$, veh vs BMN; and ** $p<0.04$, BMN vs combination; (C) graph of photon intensity in different treatment groups with days post treatment (effect of BMN and AzaC on MV4-11-luc); (D) average spleen weights; (E) % blasts in the peripheral blood in euthanized mice from different treatment groups; and (F) percentage body weight of mice in different treatment groups with time post treatment (tolerability of AzaC and BMN in systemic AML (MV4-11-luc);

FIG. 20 shows survival curves of the mice described in FIG. 20;

FIGS. 21A-21B show: (A) cytogenetic and molecular features of AML patient samples treated with DAC in combination with PARP inhibitors; and (B) cytogenetic and molecular features of cell lines treated with DAC in combination with PARP inhibitors; and FIGS. 22A-22B show Combination Index plots for MOLM14 cells treated daily for 7 days with the PARP inhibitor BMN673 (0.5, 1, 2, and 4 nM) and either DMNT1 inhibitors: (A) decitabine (5, 10, 20, 40 nM); or (B) 5-Azacytidine (50, 100, 200, 400 nM). The x-axis represents the fraction of cells affected (Fa) and the Y-axis the combination index (CI). Each point represents one combination treatment (e.g. 0.5 nM BMN and 50 nM AZA, etc). The horizontal line represents the value CI=1, where a particular drug combination is additive. Any points below the horizontal line (CI<1) represent synergistic combinations, and CI values above the line (CI>1) represent antagonistic combinations. All combinations (except 1 nM BMN/10 nM DAC and 1 nM BMN/100 nM AZA) exhibit synergism.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides methods to sensitize cells, particularly cancer cells, to poly ADP ribose polymerase (PARP) inhibitors (PARPi's) with epigenetic therapy using low doses of DNA demethylating agents. It has been found that, along with PARP inhibitors, DNA methyltransferase inhibitors (DNMTi's) also trap PARP in chromatin. The two inhibitors together increase PARP trapping, leading to inability to repair DNA damage, and leading to cell death. The presently disclosed subject matter discloses that DNMTi's bind DNA methyltransferases (DNMT's) into DNA, the DNMTi's and PARP interact, the DNMTi's therefore trap PARP into chromatin, the PARPi's trap PARP into chromatin, and that both drugs together increase further the PARP binding to chromatin as compared to each drug alone. Without wishing to be bound to any one particular theory, since PARPi's have been shown to inhibit DNA repair by increasing PARP trapping to double strand breaks, it is proposed that DNMTi's sensitize cancer cells to PARPi's by enhancing PARP trapping to chromatin and thus further decreasing DNA repair and enhancing cellular toxicity.

In some embodiments, the low doses of DNA demethylating agents sensitize cancers to poly ADP ribose polymerase (PARP) inhibitors. These demethylating agents in combination with PARP inhibitors increase cytotoxic DNA-PARP complexes in chromatin, reduce DSB repair and lead to cytotoxic cell death. In other embodiments, transient exposure to DNA demethylating agents at low nM concentrations reprograms cancer cells by altering heritable gene expression patterns in key cellular pathways, including DNA repair pathways.

I. Methods for Treating Cancer Using a DNA Demethylating Drug and a PARP Inhibitor DNA demethylating drugs, such as Vidaza (5-azacitidine; 5-AZA; 5AZA; AZA) and Dacogen (DAC), are FDA approved, but historically have been used at high doses in cancers, which have led to cytotocity of normal tissues. It has recently been shown that transient, low nM doses of DNA demethylating agents reprogram cancer cells, exerting durable anti-tumor effects on leukemia and breast cancer cells in vitro and in vivo (Tsai et al., 2012). These effects are accompanied by sustained decreases in genome wide promoter methylation, alterations in heritable gene expression patterns, and anti-tumor changes in key cellular pathways, including DNA repair pathways. These effects have already been translated for non-small cell lung cancer into actual early clinical efficacy, with a particularly strong indication that use of Vidaza after treatment with histone deacetylase inhibitors, can prime patients for robust responses to subsequent chemotherapies. The presently disclosed subject matter demonstrates that prior treatment with these epigenetic agents sensitizes cancer cells to targeted agents, such as PARP inhibitors (referred to herein interchangeably as PARPis, PARPi's, PARPi).

PARPi's impair DNA damage repair and induce cytotoxicity proportional to PARP1 trapping at DNA damage sites. The presently disclosed subject matter demonstrates that, in acute myeloid leukemia (AML) cells, DNA methyltransferase inhibitors (DNMTi's) robustly enhance this trapping and cytotoxicity. Without wishing to be bound to any one particular theory, the underlying mechanism appears that DNMT's and PARP1 interact in a DNA damage-induced complex. Low doses of DNMTi's alone trap PARP into chromatin and when combined with the PARPi, further increase PARP1 trapping, suppress DNA repair, and blunt colony, self-renewal of primary and cultured AMLs. These effects include AML cells carrying the very poor prognostic marker, FLT3/ITD mutations. Importantly, in vivo treatment with well tolerated, low doses of the drug combination blunts tumorigenesis in mice bearing engrafted human AML cells with FLT3/ITD, with reduced marrow tumor burden, spleen weights and leukemic blast cells. Thus, the presently disclosed subject matter provides a compelling, mechanism-based, therapy for cancers, such as AML, including a subtype of AML with very poor prognosis.

In some embodiments, the presently disclosed subject matter provides a method for treating a cancer, the method comprising administering to a subject in need of treatment thereof an effective amount of a low dose of a DNA demethylating agent and an effective amount of a poly ADP ribose polymerase (PARP) inhibitor.

As used herein, a DNA demethylating agent is a compound that can inhibit methylation of DNA. In some embodiments, the DNA demethylating agent is a DNA methyltransferase inhibitor (DNMTi). A DNA methyltransferase inhibitor is a compound that inhibits an enzyme that can catalyze the transfer of a methyl group to DNA. In particular embodiments, the DNMTi is selected from the group consisting of 5-azacitidine, decitabine, SGI-110 and disulfiram (a DNMT1 inhibitor).

In some embodiments, the DNA demethylating agent or PARP inhibitor can be inactive until converted to the active form in a subject. For example, the presently disclosed subject matter also encompasses inactive versions of decitabine, such as SGI-110 (Astex), which get converted to decitabine by the body.

As used herein, a poly ADP ribose polymerase (PARP) is a member of a family of proteins that is involved in a number of cellular processes, such as DNA repair and programmed cell death. A PARP inhibitor (PARPi) reduces the functioning of a PARP. In particular embodiments, the PARP inhibitor is selected from the group consisting of Veliparib, BMN-673, 4-iodo-3-nitrobenzamide, Olaparib, Rucaparib, and CEP 9722. Specific examples include, but are not limited to, ABT-888 (Veliparib), Iniparib and BSI 201 (4-iodo-3-nitrobenzamide), AZD2281 and KU-0059436 (Olaparib), and AG014699 and PF-01367338 (Rucaparib).

By "low dose" of a DNA methylating agent, it is meant a dose that is under the 1 μM range, such as less than 750 μM, less than 500 μM, or less than 100 μM. Referring to doses in m g/m$^2$, a "low dose" means doses such as less than 100 mg/m$^2$, less than 80 mg/m$^2$, less than 60 mg/m$^2$, less than 40 mg/m$^2$, or less than 20 mg/m$^2$. In some embodiments, the low dose of DNA demethylating agent is less than about 100 mg/m$^2$. In other embodiments, the low dose of DNA demethylating agent is from about 20 mg/m$^2$ to about 75 mg/m$^2$.

In some embodiments, the effective amount or dose of the PARP inhibitor is not a low dose. In other embodiments, the effective amount or dose of the PARP inhibitor is a low dose. In still other embodiments, the effective amount of the PARP inhibitor is less than about 1 mg/m$^2$ for a potent PARPi, such as BMN673, and less than about 500 mg/m$^2$ for a weaker PARPi, such as ABT888. In further embodiments, the effective amount of the PARP inhibitor is from about 1 to about 500 mg/m$^2$.

In some embodiments, the DNA demethylating agent is SGI-110 and the dosage is about 60 mg/m$^2$ or less, given subcutaneously daily for five days over a 28-day cycle. In other embodiments, the DNA demethylating agent is decitabine and the dosage is about 20 mg/m$^2$ given intravenously daily for five days over a 28-day cycle. In still other embodiments, the DNA demethylating agent is azacitidine and the dosage is about 75 mg/m$^2$ or less, given intravenously or subcutaneously daily for seven days over a 28-day cycle. In further embodiments, the PARPi is given orally days 1 through 28 over a 28-day cycle. In still further embodiments, the administration schedule comprises three days of daily administration of the DNMTi (5AZA or DAC; less than about 1 μM range), recovery 4 to 7 days, and then treatment with PARPi (ABT888, less than about 500 μM; BMN673, about 10 nM or less).

In some embodiments, the effect of the DNA demethylating agent and the poly ADP ribose polymerase (PARP) inhibitor is synergistic. As used herein, the terms "synergy," "synergistic," "synergistically" and derivations thereof, such as in a "synergistic effect" or a "synergistic combination" or a "synergistic composition" refer to circumstances under which the biological activity of a combination of the DNA demethylating agent and the poly ADP ribose polymerase (PARP) inhibitor is greater than the sum of the biological activities of the respective agents when administered individually. The synergy can occur when the respective agents are administered at the same time or if one of the agents is administered before the other.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index (SI)}$$

wherein:
$Q_A$ is the concentration of a component A, acting alone, which produced an end point in relation to component A;
$Q_a$ is the concentration of component A, in a mixture, which produced an end point;
$Q_B$ is the concentration of a component B, acting alone, which produced an end point in relation to component B; and
$Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy is that is shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

As used herein, a "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A cancer can include, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In particular embodiments, the cancer is selected from the group consisting of leukemia, myelodysplastic syndrome (MDS), breast, and ovarian. As used herein, the term "myelodysplastic syndrome" refers to a type of cancer in which the bone marrow does not make enough healthy blood cells and there are abnormal cells in the blood and/or bone marrow.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments). In other embodiments, the subject is non-human.

In some embodiments, treating of the cancer includes reducing the double-stranded DNA repair mechanism in one or more of the cancer cells in the subject. In other embodiments, treating of the cancer includes increasing the number of cytotoxic DNA-poly ADP ribose polymerase (PARP) complexes in the chromatin in one or more of the cancer cells in the subject. As used herein, the term "chromatin" refers to the macromolecules of which the chromosomes of eukaryotes are composed, comprising DNA, protein and RNA.

In some embodiments, the low dose of the DNA demethylating agent is administered prior to the effective dose of the PARP inhibitor. "Prior" may mean the DNA demethylating agent is administered minutes, hours, or days before administration of the PARP inhibitor. In other embodiments, the low dose of the DNA demethylating agent is administered simultaneously with the effective dose of the PARP inhibitor. In still other embodiments, the low dose of the DNA demethylating agent and the effective dose of the PARP inhibitor are each given in a once daily dose. The two agents may be given at the same time in the day or at different times in a day.

In any of the above-described methods, the administering of a low dose of a DNA demethylating agent and an effective dose of a PARP inhibitor can result in at least about a 10%, 15%, 20%, 25%, 30%, 35%, 40%, 45%, 50%, 55%, 60%, 65%, 70%, 75%, 80%, 85%, 90%, 95%, or even 100% decrease in the cancer in a subject.

As used herein, the terms "treat," "treating," "treatment," and the like, are meant to decrease, suppress, attenuate, diminish, arrest, the underlying cause of a cancer, or to stabilize the development or progression of a cancer and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a cancer, or partial amelioration of one or more symptoms of the cancer, and can be temporary or permanent. The term "treatment" also is intended to encompass prophylaxis, therapy and cure.

II. Methods for Sensitizing a Cell to a PARP Inhibitor

The presently disclosed subject matter also provides a method for sensitizing a cell to a poly ADP ribose polymerase (PARP) inhibitor, the method comprising contacting the cell with an effective amount of a low dose of a DNA demethylating agent prior to contacting the cell with an effective amount of the PARP inhibitor. As used herein, "sensitizing" a cell means to cause a cell to respond easier or quicker to a PARP inhibitor as compared to a cell that is not sensitized.

"Contacting" means any action that results in the low dose of the DNA demethylating agent and the effective dose of the PARP inhibitor physically contacting at least one cell. The method can be practiced in vivo, in which case contacting means exposing at least one cell in a subject to the low dose of the DNA demethylating agent and the effective dose of the PARP inhibitor, such as administering the low dose of the DNA demethylating agent and the effective dose of the PARP inhibitor to a subject via any suitable route. According to the presently disclosed subject matter, contacting may comprise introducing, exposing, and the like, the low dose of the DNA demethylating agent and the effective dose of the PARP inhibitor at a site distant to the cells to be contacted, and allowing the bodily functions of the subject, or natural (e.g., diffusion) or man-induced (e.g., swirling) movements of fluids to result in contact of the low dose of the DNA demethylating agent and the effective dose of the PARP inhibitor and cell(s).

In some embodiments, the DNA demethylating agent is a DNA methyltransferase inhibitor (DNMTi). In other embodiments, the DNMTi is selected from the group consisting of 5-azacitidine, decitabine, SGI110 and disulfiram. In still other embodiments, the PARP inhibitor is selected from the group consisting of Veliparib, BMN-673, 4-iodo-3-nitrobenzamide, Olaparib, Rucaparib, and CEP 9722. In further embodiments, the low dose of DNA demethylating agent is less than about 1 µM. In still further embodiments, the effective dose of PARP inhibitor is less than about 500 µM. In some embodiments, the effect of the DNA demethylating agent and the PARP inhibitor is synergistic.

In some embodiments, the cell is a cancer cell. In other embodiments, the cancer cell is selected from the group consisting of a leukemia, myelodysplastic syndrome (MDS), breast, and ovarian cell. In still other embodiments, the leukemia is acute myeloid leukemia (AML). In further embodiments, the AML is FLT3-ITD positive.

III. Methods for Reducing Repair of Double-Strand Breaks in DNA in a Cell

In some embodiments, the presently disclosed subject matter provides a method for reducing repair of double-strand breaks in DNA in a cell, the method comprising contacting the cell with an effective amount of a low dose of a DNA demethylating agent and with an effective amount of a poly ADP ribose polymerase (PARP) inhibitor.

In some embodiments, the DNA demethylating agent is a DNA methyltransferase inhibitor (DNMTi). In other embodiments, the DNMTi is selected from the group consisting of 5-azacitidine, decitabine, SGI-110 and disulfiram.

In still other embodiments, the PARP inhibitor is selected from the group consisting of Veliparib, BMN-673, 4-iodo-3-nitrobenzamide, Olaparib, Rucaparib, and CEP 9722.

In some embodiments, the low dose of DNA demethylating agent is less than about 1 μM. In other embodiments, the effective dose of PARP inhibitor is less than about 500 μM. In still other embodiments, the effect of the DNA demethylating agent and the PARP inhibitor is synergistic.

As used herein, the term "reduce" means to decrease, suppress, attenuate, diminish, or arrest, e.g., by at least 10%, 20%, 30%, 40%, 50%, 60%, 70%, 80%, 90%, 95%, 98A %, 99%, or even 100% compared to an untreated control subject, cell, or biological pathway.

IV. Methods for Increasing Cytotoxic DNA-Poly ADP Ribose Polymerase (PARP) Complexes in a Cell The presently disclosed subject matter discloses the use of DNA demethylating agents in combination with PARP inhibitors to enhance the production of or increase the number of cytotoxic DNA-PARP complexes in chromatin, which leads to cytotoxic cell death. Accordingly, in some embodiments, the presently disclosed subject matter provides a method for increasing cytotoxic DNA-poly ADP ribose polymerase (PARP) complexes in a cell, the method comprising contacting the cell with an effective amount of a low dose of a DNA demethylating agent and with an effective amount of a PARP inhibitor.

In some embodiments, the DNA demethylating agent is a DNA methyltransferase inhibitor (DNMTi). In other embodiments, the DNMTi is selected from the group consisting of 5-azacitidine, decitabine, SGI-110 and disulfiram. In still other embodiments, the PARP inhibitor is selected from the group consisting of Veliparib, BMN-673, 4-iodo-3-nitrobenzamide, Olaparib, Rucaparib, and CEP 9722.

In some embodiments, the low dose of DNA demethylating agent is less than about 1 μM. In other embodiments, the effective dose of PARP inhibitor is less than about 500 μM. In still other embodiments, the low dose of the DNA demethylating agent is administered prior to the PARP inhibitor. In further embodiments, the low dose of the DNA demethylating agent is administered simultaneously with the PARP inhibitor. In still further embodiments, the effect of the DNA demethylating agent and the PARP inhibitor is synergistic.

As used herein, the term "increase" means to become or make greater in size, amount, intensity, or degree, e.g., by at least 10%, 20%, 30%, 40%, 50%, 60%, 70%, 80%, 90%, 95%, 98A %, 99%, or even 100% compared to an untreated control subject, cell, or biological pathway. In particular embodiments, the presently disclosed subject matter provides a method for increasing the number of cytotoxic DNA-poly ADP ribose polymerase (PARP) complexes in a cell.

V. Administration of Pharmaceutical Compositions

The term "administering" as used herein refers to contacting a cell or portion thereof with a low dose of the DNA demethylating agent and an effective dose of the PARP inhibitor. This term includes administration of the presently disclosed compounds to a subject in which the cell or portion thereof is present, as well as introducing the presently disclosed compounds into a medium in which a cell or portion thereof is cultured. In some embodiments of the presently disclosed methods, the low dose of the DNA demethylating agent and the effective dose of the PARP inhibitor are administered in combination with one or more additional therapeutic agents.

Administration to a subject for therapy can occur by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eye drops), including buccally and sublingually, transdermally, through an inhalation spray, or other modes of delivery known in the art.

The phrases "systemic administration," "administered systemically," "peripheral administration" and "administered peripherally" as used herein mean the administration of the low dose of the DNA demethylating agent and the effective dose of the PARP inhibitor other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion. In particular embodiments, administration of the DNA demethylating agent and the PARP inhibitor occur by subcutaneous or intravenous administration.

By "in combination with" is meant the administration of the low dose of the DNA demethylating agent and the effective dose of the PARP inhibitor with each other or with one or more other therapeutic agents either simultaneously, sequentially, or a combination thereof. The low dose of the DNA demethylating agent and the effective dose of the PARP inhibitor can be administered with one or more other therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the low dose of the DNA demethylating agent and the effective dose of the PARP inhibitor and one or more other therapeutic agents are administered simultaneously, they can be administered to the cell or administered to the subject as separate pharmaceutical compositions, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a cancer), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

VI. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

DNMT Inhibitor-Dependent Sensitization of Leukemia Cells to PARP Inhibition

Methods

Cell culture, drugs and treatment schedule and doses: Human AML cells KASUMI-1 (AML1-ETO positive) were cultured in RPMI1640+L-Glutamine (Life technologies Gibco®, Grand Island, N.Y.), supplemented with 20% Fetal Bovine Serum (FBS, Sigma-Aldrich Co., St. Louis, Mo.); MV411 (homozygote for FLT3-ITD), MOLM14 (heterozygote for FLT3-ITD) were cultured in RPMI1640+L-Glutamine supplemented with 10% FBS. Isolation of bone marrow or blood mononuclear cells (MNC) from AML samples was accomplished using Histopaque-1077 (Sigma-Aldrich) according to the instructions of the manufacturer and MNC were incubated overnight in hematopoietic progenitor growth media (HPGM, Lonza, Walkersville, Md.) supplemented with 50 ng/mL thrombopoietin and FLT3 Ligand, 25 ng/ml stem cell factor, 10 ng/mL Interleukin-3 (IL-3), IL-6, Granulocyte macrophages-colony stimulating factor (GM-CSF) and 1 ng/mL G-CSF (Gemini Bio Product, West Sacramento, Calif.). Provision of all primary AML was through protocols approved by the institutional review boards at the University of Maryland School of Medicine (IRB # H25314). All cell lines and MNC were initially cultured at $0.2 \times 10^6$ cells/mL and $0.5 \times 10^6$ cells/mL respectively, at 37° C. and 5% $CO_2$.

Decitabine (DAC, 21.9 mM in DMSO, Sigma-Aldrich) was further diluted in water just before treatment of the cells with 5 nM, 10 nM or 20 nM of DAC. PARPi's Veliparib (ABT888; 200 mM in water, A Life Sciences Alexis, Farmingdale, N.Y.) and BMN673 (10 mM in DMSO, Abmole BioScience, Kowloon, Hong Kong) were further diluted in water just before treatment of the cells with 500 nM of ABT888 and 1 nM, 10 nM or 100 nM of BMN673. DAC was added every 24 hours for 72 hours with daily medium change, then the drug was washed out and cells were allowed to recover for 4 days (unless indicated otherwise) before further use. At day 7, cells were counted with trypan blue, treated with PARPi's, set in culture in 100 mm plates at a density of $0.2 \times 10^6$ cells/mL or in methylcellulose for colony forming assay as described later. At days indicated on the figures, 5- to $10 \times 10^6$ viable cells (trypan blue exclusion) were recovered, fast frozen and stored at $-80°$ C. for further use for protein extraction. A representative protocol is shown in FIG. 1.

Colony forming assay: At Day 7 of the experiment, equal numbers of viable cells (KASUMI-1 cells, 10000 cells/dish; MV411, 5000 cells/dish; MOLM14, 1000 cells/dish; Patients #16, 2000 cells/dish, #9, #13 and #15, 5000 cells/dish, #29, 10000 cells/dish, #30, 20000 cells/dish and #34, 40000 cells/dish) were treated as described earlier and plated in triplicate in 33 mm dish on MethoCult H4435 Enriched (StemCell Technologies, Vancouver, British Columbia, Canada) for MNC, or Methylcellulose Stock Solution (R&D Systems, Minneapolis, Minn.) supplemented with culture media for cell lines according to the instructions of the manufacturer. Ten to nineteen days later, colonies were stained with 2-(4-iodophenyl)-3-(4-nitrophenyl)-5-phenlytetrazolium chloride (1 mg/mL) overnight at 37° C. and colonies containing more than 40 cells were quantified using a colony counter and Protocol3 software (Synbiosis, Frederick, Md.). Results (fold changes compared to CRTL treatment) are representative of the mean±SEM of at least two independent experiments in triplicate.

Cell proliferation/cytotoxicity assay: Cells (20000 cells/well in 200 μL) were grown in 96-well plates with ABT888 or BMN673 (up to 10 μM) for 72 hours. Four hours prior to evaluation, 20 μL of MTS labelling reagent ([3-(4, 5-dimethylthiazol-2-yl)-5-(3-carboxymethoxyphenyl)-2-(4-sulfophenyl)-2H-tetrazolium, MTS supplemented with phenazine methosulfate, PMS, Promega, Madison, Wis.) was added to each well. The results were quantified using a VersaMax Elisa Microplate Reader at a wavelength of 490 nm and SoftMax®Pro software (Molecular Devices, Sunnyvale, Calif.). Results (fold changes compared to CRTL) are representative of the mean±SEM of three independent experiments in triplicate.

Statistical analysis: All statistical analyses were performed using a Student T-test with * meaning p value <0.05 unless indicated otherwise.

Results

Figure 2B:
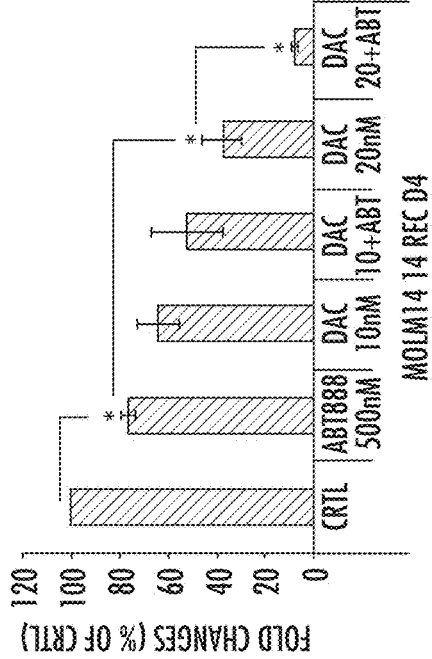
Figure 2D:
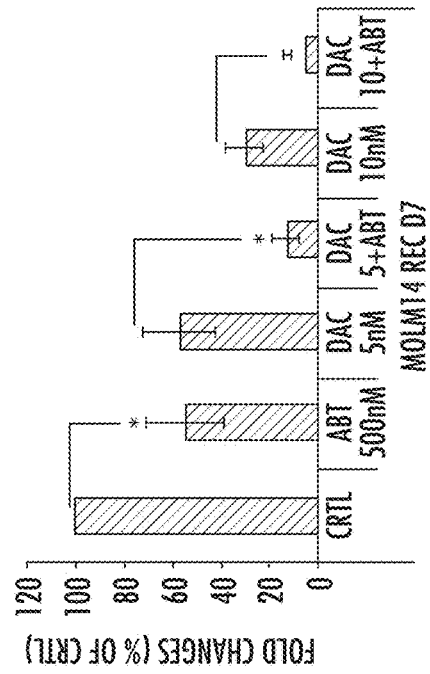
Figure 2A:
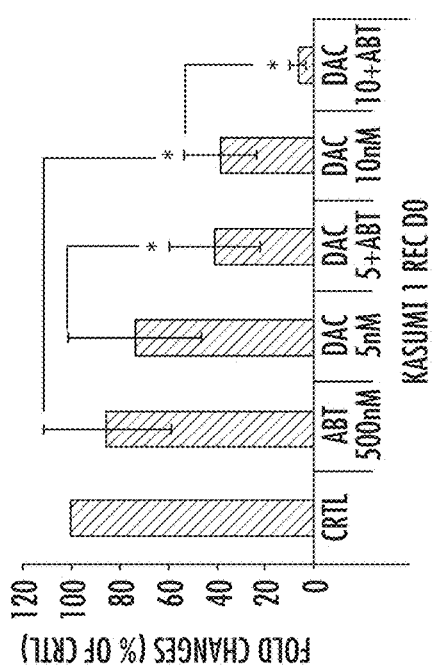
Figure 2C:
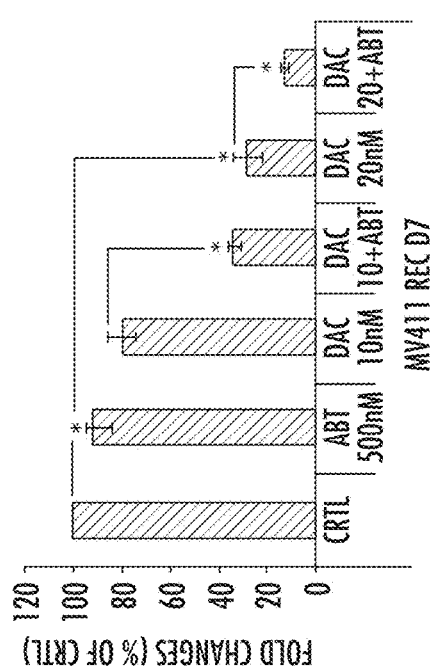
Figure 3A:
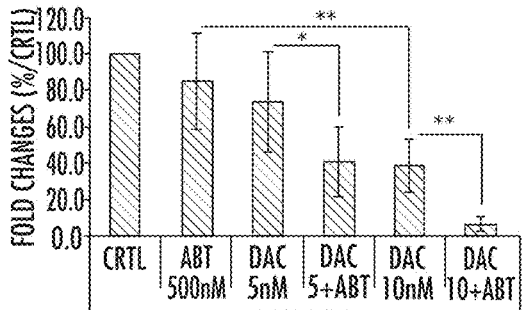
Figure 3B:
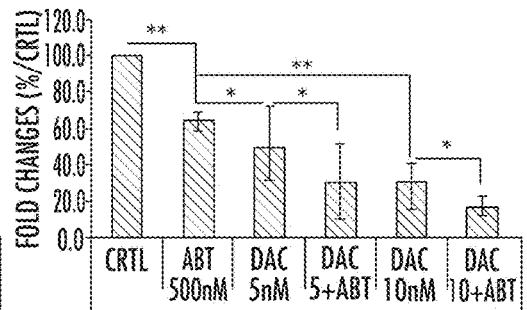
Figure 3C:
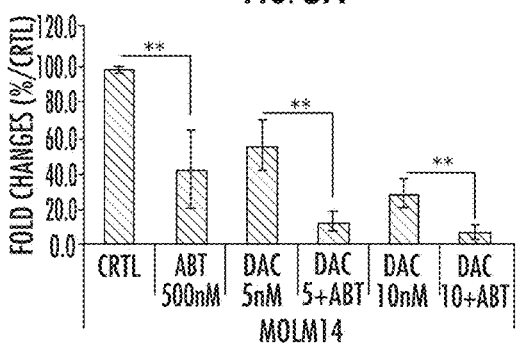
Figure 3D:
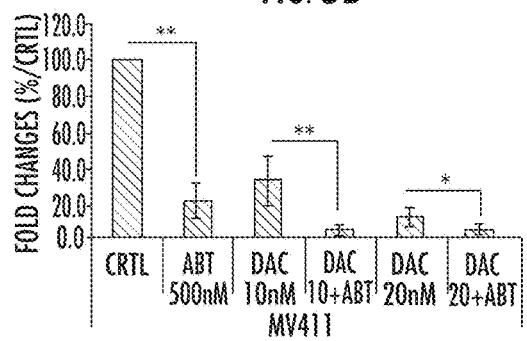
Figure 3E:
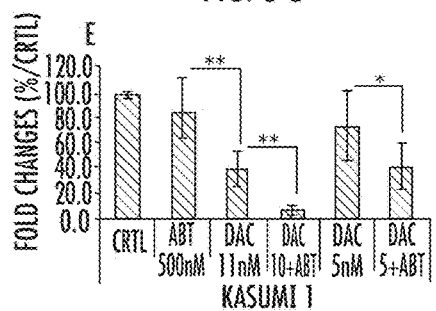
Figure 3F:
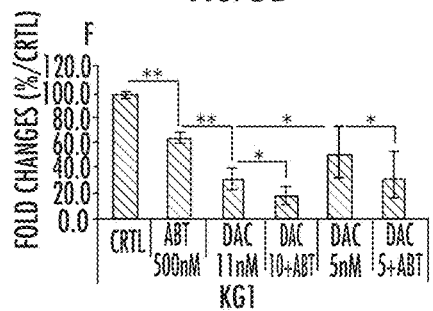
Figure 3G:
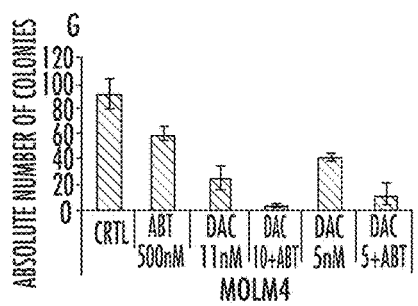

In order to study if the DAC dependent reprogramming (Tsai et al., 2012) could sensitize AML cells to PARPi's, KASUMI-1, MOLM14 and MV411 cells were first treated with increased doses of DAC (5 nM-20 nM) for three days with daily replacement of drugs and media as described previously (Tsai et al., 2012). Thereafter, cells were grown without drugs for 0 days to 7 days, the number of days without drug varied between each line, depending on the sensitivity of each cell line to DAC. Following the rest period, the same amount of viable cells were plated on methylcellulose under continuous treatment with PARPi ABT888 (500 nM) as previously described (Tobin, 2013) (FIG. 2). Ten days later, clonogenic efficiency was measured by counting colonies with more than 40 cells and results were expressed as fold changes compared to controls (CRTL) (FIG. 2). Treatment of cells with DAC as a single agent showed that KASUMI-1 cells were the most sensitive, demonstrating a significant decrease in colony number after 10 nM of DAC (FIG. 2A). MOLM14 and MV411 cells showed a similar decrease in colonies but only after treatment with 20 nM of DAC (FIGS. 2B-2C). Treatment of PARPi ABT888 as a single agent showed that FLT3-ITD-positive MOLM 14 and MV411 cells had a significant reduction of colony numbers compared to CRTL, while KASUMI-1 cells were not significantly affected. Notably, pretreatment of the AML cell lines with DAC followed by ABT888 led to a significantly reduced number of colonies, compared to ABT888 or DAC treatment alone (FIGS. 2 and 3). It was found that no recovery days between the addition of DAC and ABT888 was not as effective as recovery for 7 days (FIG. 4).

These results first confirmed that FLT3-ITD positive AML cells were sensitive to PARPi's alone as suggested earlier (Gaymes et al., 2013; Gaymes et al., 2009), but more interestingly demonstrated that pre-treatment with a non-cytotoxic low dose of DNMTi's (Tsai et al., 2012) such as DAC could sensitize AML cells (AML1-ETO or FLT3-ITD) to a low dose of PARPi's. Therefore, this combinatorial treatment is a new therapeutic for AML patients.

BMN673 is more cytotoxic to AML cells than ABT888: PARPi's has been shown to selectively kill tumors harboring DSB repair deficiency such as the mutation in BRCA1/2 in the homologous recombination repair pathway (Bryant et al., 2005; Helleday et al., 2005) inducing a "synthetic lethality" (Farmer et al., 2005) suggesting the use of PARPi's in other tumors with DSB repair abnormalities (Ashworth et al., 2008). These findings have led to the development of more specific and potent PARPi's (Murai et al., 2013; Shen et al., 2013). Recently, BioMarin developed a new PARPi, BMN673, which is more potent in killing DNA repair deficient breast and ovarian cancer cells than any other PARPi's (Shen et al., 2013). Thus, BMN673 is now tested in clinical trials for the treatment of patients with solid tumors (Shen et al., 2013). To determine whether pre-treatment with DAC sensitizes AML to BMN673, the MTS assay was first used to determine the concentrations of BMN673 and ABT888 that induced cytotoxicity in FLT3-ITD-positive cell lines MOLM14 and MV411 (FIG. 5). In MV411 and MOLM14, BMN673 had an IC50 of 6.45 μM and 4.46 μM, respectively. In contrast, the IC50 of ABT888 was >25 μM (FIG. 5). These results are in line with previous results showing that MOLM14 is more sensitive to PARPi ABT888 than MV411. Notably, BMN673 is much more potent than ABT888 in AML cell lines which is similar to findings in other cancers (Shen et al., 2013).

BMN673 potently inhibits clonogenicity in AML cell lines and its effect is potentiated by pre-treatment with DAC: Given that BMN673 is much more potent than ABT888, the question was whether above AML cell lines pretreated with DAC would also sensitize to BMN673. Therefore, FLT3-ITD MOLM14 and MV411 cell lines were pretreated for 3 days with DAC (20 nM), followed by a recovery period of 4 days, subsequent treatment with BMN673 (1 nM, 10 nM and 100 nM), and clonogenic assays in methylcellulose were performed (FIG. 6). As expected, treatment between 10 nM and 100 nM of BMN673 profoundly inhibited colony formation in MOLM14 (FIG. 6A) and MV411 (FIG. 6B). Similar to results with ABT888, MOLM14 cells were more sensitive to BMN673, with cytotoxicity occurring following 1 nM drug treatment, compared to MV411 cells which were barely sensitive at this concentration. Nevertheless, pretreatment with 20 nM DAC rendered MOLM14 cells significantly more sensitive to 1 nM of BMN673, compared to DAC or BMN673 treatment alone. While experiments with MV411 cells showed sensitivity to BMN673 at all concentrations tested, pre-treatment with 20 nM DAC did not sensitize these cells further to BMN673.

Primary cells from AML patients are sensitive to the combination DAC and PARPi's: AML is a heterogeneous disease and therefore it was determined whether primary samples from AML patients pretreated with DAC were also sensitized to treatment with PARPi's. Therefore, treated MNCs from 6 AML patients (#9, #15, #29, #16, #30 and #34) were pretreated for 3 days with DAC (10 nM-20 nM), followed by 4 days of recovery and final plating of cell in methylcellulose in the presence of ABT888 (500 nM; FIG. 7A). Only MNCs from patient #34 were pretreated with DAC followed by treatment with BMN673 (1 nM; FIG. 7B). Three of 6 patients (Patient #15, #29, #16; 50% responders) showed variably decreased colony number with PARPi ABT888 treatment alone. All samples showed decreased colonies with DAC treatment alone and, in fact, MNCs from patient #9 appeared highly sensitive. Importantly, MNCs from 4 of 6 patients (Patients #9, #15, #29, and #34; 67%) showed that pretreatment with DAC further sensitized to ABT888 treatment (FIG. 7A). Moreover, similar to MOLM14 and MV411 cells, patients #15, #29 and #34 were FLT3-ITD-positive, validating the effects of DAC plus PARPi treatment in this unfavorable molecular sub-group of AML (FIG. 7A). Similar to results with DAC plus ABT888, MNCs from patient #34 showed that pretreatment with DAC also sensitized the cells to BMN673 treatment (1 nM, FIGS. 7B,7C). Cells from patients #16 and #29 also showed similar results (FIG. 7C). FIG. 8 shows analysis of the sample from patient #29 in more detail including Western blot analysis of ubiquitin (UB), DNA methyltransferase 1 (DNMT1), PARP1, and Caspase 3 of total extract of bone marrow mononuclear cells (BMMNC) (FIG. 8A), and ELISA assays measuring total level of poly-(ADP)-ribose (pADP) in BMMNC (FIGS. 8B-8C). These results showed that clonogenicity was decreased by DAC and further decreased by DAC and ABT888 in bone marrow mononuclear cells of patient #29. FIGS. 9A-9D show that AML cell lines MOLM14 and MV411 and primary cells from patients #29 and #34 were more sensitive to a combination of DAC and BMN673 as compared to each compound alone.

These results in cell lines and primary cells show that AML, and in particular FLT3-ITD positive AMLs, pretreated with DAC further sensitize to treatment with PARPi's, suggesting a potential therapeutic strategy with administration of DNA methyltransferase inhibitors (DNMTi's) followed by a PARP DNA repair inhibitor (PARPi's).

Multiple cancer cell lines derived from leukemia, breast, ovarian, and lung were treated with low dose DAC/5-AZA (10 nM and 5 nM) for 3 days, followed by removal of the drug for 4 days to 7 days, and subsequent plating of cells in methylcellulose to follow self-renewal capability in the presence or absence of the PARP inhibitor ABT888 (500 nM). Results showed that treatment with DAC/5/AZA alone produces a significant decrease in colony numbers, while PARP treatment alone has an effect in some cases (FIGS. 10 and 11). However, both drugs used consecutively significantly reduce colony growth even further than for DAC or ABT888 alone.

Discussion

These results suggest that demethylating agents can alter the function of PARP targets, leading to the enhanced effect of the inhibitors. Both 5AZA and ABT888 treatment alone decreases PARP activity and steady state levels of key double strand break repair proteins including expression levels of PARP1 itself, suggesting that one of the mechanisms for DAC sensitization of AML cells to PARP inhibitors is through altering the repair of DSBs. PARP1 appears to be bound in a complex with methylating agents DNA methyltransferase 1 (DNMT1) following DNA damage, suggesting a novel mechanism for the combined effects of demethylating agents and PARP inhibitors on cancer cells. Without wishing to be bound to any one particular theory, iIn this scenario, DNMTi's, such as Vidaza, Dacogen, and SGI-110, to function as DNA demthylating agents, must incorporate into DNA as an altered cytosine where they then must bind DNMT's into DNA to block the enzymatic activity of these proteins. Because DNMT's and PARP interact, it is shown that DNMTi's, alone, trap PARP into chromatin. PARPi's also trap PARP into chromatin at DNA double strand breaks, and both drugs together increase further the PARP binding to chromatin as compared to each drug alone. Since PARPi's have been shown to inhibit DNA repair through increasing PARP trapping to double strand breaks, this is the proposed mechanism by which DNMTi's sensitize cancer cells to PARPi's by their enhancing PARP trapping to chromatin—and thus further decreasing DNA repair and enhancing cellular toxicity.

Prior studies demonstrated increased levels of Poly-(ADP)-ribose polymerase (PARP1) as well as increased activity of a highly error-prone pathway for repair of DNA double-strand breaks (DSBs) in myeloid leukemia. In addition, recent studies have shown that transient exposure to DNA demethylating agents (DNMTi's), such as decitabine (DAC) or azacitidine (AZA), at low nM concentrations reprograms cancer cells, including breast cancer and AML, altering heritable gene expression patterns in key cellular pathways, including DNA repair pathways. These studies show that pre-treatment of leukemia cells and breast cancer cells with demethylating agents can further sensitize them to PARP inhibitors (PARPi's).

Thus, established cell lines from AML (MOLM14, MV411, KASUMI-1), and mononuclear cells (MNC) obtained from bone marrow or blood patient samples (N=6) were exposed to non-cytotoxic doses of DNMTi's, followed by four days without drug exposure and subsequent treatment with PARPi's (less potent ABT888, or highly potent BMN673). In all the cell lines tested, treatment with DAC (5 nM-10 nM) followed by ABT888 (500 nM) induced a significant decrease in colony survival compared to control or single treatment. The use of PARPi, BMN673 (0.1 nM-100 nM), confirmed that treatment with DNMTi's followed by PARPi's induces a robust and significant inhibition of AML cell line colony forming capacity. Importantly, the same schedule treatment of DAC followed by PARPi's significantly decreases the clonogenic capacity in 4 out of 6 (67%) of MNC from AML patients tested, suggesting that sequential treatment of DNMTi's and PARPi's is a therapeutic option for AML and particularly for FLT3-ITD positive AML malignancies from which multiple cell lines and patient samples examined were derived. This treatment strategy also can be applicable to breast and ovarian cancers As shown, decitabine and PARP inhibitors (ABT888 and BMN673) participate together in decreasing clonogenicity in AML cell lines. At the doses used, neither apoptosis nor proliferation blockage could totally explain the decrease in clonogenicity. Decitabine decreased PARP1 levels through possible activation of the proteasome and this effect was increased in the presence of PARP inhibitors (ABT888 and BMN673). Also, in the presence of damage, PARP inhibitors increased the presence of PARP at the chromatin creating cytotoxic PARP-DNA complexes.

Preliminary results show a mechanism of action by which DAC treatment leads to PARP localization on chromatin and subsequent PARPi's treatment resulting in increased trapping of PARP. As expected, in immunoblotting assays, DAC treatment alone was sufficient to decrease DNMT1 expression levels and increase caspase 3 cleavage in AML cell lines, compared to control treated cells. Surprisingly, DAC treatment alone also induced a decrease in PARP protein expression, with a further decrease in cells treated with DAC followed by PARPi's, suggesting that both methylation and DNA repair signaling alter PARP1 steady-state levels. Moreover, preliminary results show that the presence of PARP on chromatin is decreased with DAC treatment and further decreased following PARPi's.

In summary, these results suggest that DNMTi's reprogram cells, sensitizing them to PARP inhibition in AML/MDS patient and cell line models, paving the way for testing the therapeutic potential of sequential treatment with these agents in clinical trials. Understanding how these proteins interact may explain the mechanisms underlying the sensitization of epigenetically reprogrammed cells to PARPi's, and may define the molecular subsets of AML patients that may respond to this novel therapeutic strategy.

Example 2

Enhancing the Cytotoxic Effects of PARP Inhibitors by DNA Demethylating Agents

A Potential Therapy for Acute Myeloid Leukemia (AML)

Introduction

In some aspects, the presently disclosed subject matter introduces a mechanism-based therapy paradigm employing DNA methyltransferase (DNMTi's) and PARP inhibitors (PARPi's) that provide a compelling treatment approach to acute myeloid leukemia (AML), including a very therapy resistant subtype. AML is a heterogeneous disease subdivided into cytogenetic and molecular subsets characterized by favorable and unfavorable responses to current therapies (Bullinger et al., 2008). Present studies include work with one of the most unfavorable subsets, AML with Fms-like tyrosine kinase 3 internal tandem duplications (FLT3/ITD), a constitutively active tyrosine kinase expressed in 30% of all AML cases (Bullinger et al., 2008). Over the last three decades, clinical efforts have been made to improve the outcome of AML patients mostly by increasing the intensity of chemotherapy. Adult patients and those with therapy-related AML (t-AML) and relapsed or refractory AML continue to have poor outcomes, with less than 10% achieving long-term survival, underscoring the urgent need for new therapeutic strategies (Bullinger et al., 2008).

AML is characterized by genomic instability and a dependency on repair of resultant DNA damage by pathways involving PARP family proteins. These pathways include error-prone repair of double strand breaks (DSBs), which are the most lethal form of DNA damage and which can be repaired by two main pathways in mammalian cells (i) error free, homologous recombination (HR) that uses sister chromatids as template or (ii) error prone non-homologous end-joining (NHEJ) that joins DNA ends irrespective of their origins and functions throughout the cell cycle. FLT3/ITD-expressing AML cells, particularly, demonstrate enhanced activity of an alternative and highly error-prone form of NHEJ (ALT NHEJ) and, important to the present work, concomitant increases in levels of the key constituent, PARP1. PARP1 is an abundant nuclear protein that senses, and is involved in the repair of, single strand breaks (SSBs) through use of topoisomerase I cleavage complexes that mediate base excision repair (BER; Durkacz et al., 1980). PARP1 also is active in repair of double strand breaks (DSBs) working through its action to catalyze poly-ADP-ribosylation of itself, histones and other target proteins (Hassa and Hottiger, 2008; Rouleau et al., 2010). Blocking the catalytic activity of PARP1 has been shown to inhibit base excision repair (BER), resulting in accumulation of SSBs, as well as DSBs during replication, and this damage in turn activates homologous recombination (HR).

Based on the above roles of PARP, PARPi's have been used successfully to sensitize HR deficient cancer cells to cytoxocity in vitro and are now being tested in clinical trials. Importantly, the cytotoxic effect of PARPi's has been correlated not with catalytic inhibition of PARP1, but with trapping of cytotoxic DNA-PARP complexes at sites of DNA damage. New more potent classes of PARP inhibitors, such as BMN673 (BioMarin) have been developed, which have up to 100-fold more inhibitory activity than earlier classes of PARPi's and this potency correlates with a much increased ability to trap PARP-1-DNA complexes compared with weaker PARPi's, such as veliparib (ABT888; Shen et al., 2013).

The presently disclosed subject matter combines the use of DNA methyltransferases inhibitors (DNMTi's), such as azacitidine (AZA) and decitabine (DAC), to enhance the above PARP trapping in AML cells. DNMTi's are now used in the clinic for the treatment of AMLs and are approved by the Food and Drug Administration (FDA) for the treatment of myelodysplastic syndromes (MDS). There is past evidence for interaction of DNMT's with PARP1 (Caiafa et al., 2009), and the present investigation provides further evidence of the interaction of these proteins in chromatin following DNA damage. The prerequisite action of DNMTi's is to trap DNMT's into DNA. It is hypothesized herein that these agents might thus enhance PARP trapping into chromatin as well (FIG. 13).

Methods

Cell culture, drugs and treatment schedule and doses: Human AML cells KASUMI-1 (AML1-ETO positive) were cultured in RPMI1640+L-Glutamine (Life technologies Gibco®, Grand Island, N.Y., supplemented with 20% Fetal Bovine Serum (FBS, Sigma-Aldrich Co, St. Louis, Mo.); MV411 (homozygote for FLT3-ITD), MOLM14 (heterozygote for FLT3-ITD) were cultured in RPMI1640+L-Glutamine supplemented with 10% FBS. Isolation of bone marrow or blood mononuclear cells (MNC) from AML samples was accomplished using Histopaque-1077 (Sigma-Aldrich) according to the instructions of the manufacturer and MNC were incubated overnight in hematopoietic progenitor growth media (HPGM, Lonza, Walkersville, Md.) supplemented with 50 ng/mL thrombopoietin and FLT3 Ligand, 25 ng/mL stem cell factor, 10 ng/mL Interleukin-3 (IL-3), IL-6, Granulocyte macrophages-colony stimulating factor (GM-CSF) and 1 ng/mL G-CSF (Gemini Bio Product, West Sacramento, Calif.). Provision of all primary AML was through protocols approved by the institutional review boards at the University of Maryland School of Medicine (IRB # H25314). All cell lines and MNC were initially cultured at $0.2 \times 10^6$ cells/mL and $0.5 \times 10^6$ cells/mL respectively, at 37° C. and 5% $CO_2$.

Decitabine (DAC, 21.9 mM in DMSO, Sigma-Aldrich) was further diluted in water just before treatment of the cells with 5 nM, 10 nM or 20 nM of DAC. PARPi's Veliparib (ABT888; 200 mM in water, Enzo Life Sciences Alexis, Farmingdale, N.Y.) and BMN673 (10 mM in DMSO, Abmole BioScience, Kowloon, Hong Kong) were further diluted in water just before treatment of the cells with 500 nM of ABT888 and 1 nM, 10 nM or 100 nM of BMN673. DAC was added every 24 hours for 72 hours with daily medium change, then the drug was washed out and cells were let to recover for 0 days to 7 days before further use. The number of days without drug varied between each cell line, depending on their sensitivity to DAC. At day 7, cells were counted with trypan blue, treated with PARPi's, set in culture in 100 mm plates at a density of $0.2 \times 10^6$ cells/mL or in methylcellulose for colony forming assay as described later. At days indicated on the figures, 5- to $10 \times 10^6$ viable cells (trypan blue exclusion) were recovered, fast frozen and stored at $-80°$ C. for further use for protein extraction. For combination treatments, drugs were administered simultaneously for the same total time length as for sequential treatments.

Colony forming assay: At Day 7 of experiment, equal numbers of viable cells (KASUMI-1 cells 10000 cells/dish; MV411 3000 cells/dish; MOLM14 1000 cells/dish; Patients #16, 2000 cells/dish, #9, #13 and #15, 5000 cells/dish, #29, 10000 cells/dish, #30, 20000 cells/dish and #34, 40000 cells/dish) were treated as described earlier and plated in triplicate in 33 mm dish on MethoCult H4435 Enriched (StemCell Technologies, Vancouver, British Columbia, Canada) for MNC, or Methylcellulose Stock Solution (R&D Systems, Minneapolis, Minn.) supplemented with culture media for cell lines according to the instructions of the manufacturer. Ten to nineteen days later, colonies were stained with 2-(4-iodophenyl)-3-(4-nitrophenyl)-5-phenlytetrazolium chloride (1 mg/mL) overnight at 37° C. and colonies containing more than 40 cells were quantified using colony counter and Protocol3 software (Synbiosis, Frederick, Md.). Results (Fold changes compared to CRTL treatment) are representative of the mean±SEM of at least two independent experiments in triplicate.

Cell proliferation/cytotoxicity assay: Cells (20000 cells/well in 200 µL) were grown in 96-well plates with ABT888 or BMN673 (up to 10 µM) for 72 hours. Four hours prior to evaluation, 20 µL of MTS labelling reagent ([3-(4,5-dimethylthiazol-2-yl)-5-(3-carboxymethoxyphenyl)-2-(4-sulfophenyl)-2H-tetrazolium, MTS supplemented with phenazine methosulfate, PMS, Promega, Madison, Wis.) was added to each well. The results were quantified using a VersaMax Elisa Microplate Reader at a wavelength of 490 nm and SoftMax®Pro software (Molecular Devices, Sunnyvale, Calif.). Results (Fold changes compared to CRTL) are representative of the mean±SEM of three independent experiments in triplicate.

Irradiation: For irradiation (IR) studies, cells were exposed to 4Gy X-Ray radiation using a Pantak HF320 X-Ray machine (250 kV peak, 13 mA; half-value layer, 1.65 mm copper) at a dose rate of 2.4 Gy/min. After IR, cells were allowed to recover from DNA damage for 4 hrs before extraction of protein.

Subcellular fractionation: To isolate the chromatin bound fraction (CH) and soluble nuclear fraction (NUC), a Subcellular Protein Fractionation kit (Thermo Fisher Scientific, Waltham, Mass.) was used by following the instructions of the manufacturer. For the DNA repair assay, NUC and CH were combined to form nuclear extract (N).

Immunoblotting: Immunoblotting was performed following standard procedures using 5 µg of NUC and CH fractions. Proteins were loaded onto a 4%-20% SDS-PAGE gel (Bio-Rad laboratories, Hercules, Calif.), transferred on PVDF membrane (GE Healthcare Life Sciences, Pittsburgh, Pa.) and blots were washed in Tris Buffered Saline-0.1% Tween 20 (TBST) three times, blocked in TBST-5% bovine serum albumin (TBST-BSA) for an hour at least and first antibodies in TBST-BSA were applied overnight at 4° C. on shaker. Blots were washed again 3 times and secondary antibodies, anti-Mouse-horse radish peroxidase (HRP; Cell signaling, Danvers, Mass.), anti-Rabbit-HRP (BioLegend, San Diego, Calif.), or alkaline phosphate (AP; Bio-Rad) in TBST were applied for an hour followed by 3 washes and detection of HRP using enhanced chemiluminescence or alkaline phosphatase using 5-bromo-4-chloro-3-indolyl-phosphate/nitro blue tetrazolium (BCIP/NBT; Promega). Antibodies used were PARP1 mouse monoclonal (1:3000, C2-10, BD Biosciences), DNMT1 mouse monoclonal (1:5000, Imgenex, San Diego, Calif.), Caspase 3 Rabbit polyclonal (1:1000, Cell Signaling), H3 rabbit polyclonal (1:30000, Sigma-Aldrich), γH2AX (1:500, EMD Millipore, Billerica, Mass.) and β-actin mouse monoclonal (1:5000, Sigma-Aldrich).

Immunofluorescence: AML cells ($0.2 \times 10^6$ cells) were cytospun onto glass slides for 5 min at 200 rpm in PBS 1× on a Shandon Cytospin 4. Cells were then fixed for 30 min in 4% paraformaldehyde, washed 3 times in DPBS (+CaCl$_2$ and MgCl$_2$, DPBS++), permeabilized for 10 min in permeabilization solution (50 mM NaCl, 3 mM MgCl$_2$, 10 mM HEPES, 200 mM Sucrose and 0.5% Triton X-100 in PBS 1×), washed 3 times in DPBS (+CaCl$_2$, +MgCl$_2$) supplemented with BSA 1% (DPBS-BSA) and then blocked overnight in DPBS++ supplemented with 10% serum. After incubation with mouse monoclonal anti-γH2A.x (1:100, Upstate), rabbit polyclonal anti-RAD51 (1:100, Santa Cruz Biotechnologies, Dallas, Tex.), rabbit Poly-ADP-ribose (PAR, 1:200, Axxora, Farmingdale, N.Y.), or isotypes controls for an hour at 37° C. in DPBS-BSA, cells were washed and then incubated with Dylight 594-anti-mouse and Dylight 488-anti rabbit (1:200, KPL, Gaithersburg, Md.) for an hour at 37° C. prior to counterstaining with 4',6 diamidino-2-phenylindole, dihydrochloride (DAPI, 0.3 µg/mL, Promega, Madison, Wis.) in mounting media (Vectashield, Vector Laboratories, Burlingame, Calif.). Slides were examined using a Nikon fluorescent microscope Eclipse 80i (100×/1.4 oil, Melville, N.Y.). Images of at least 50 cells/slide were captured using a CCD (charge-coupled device) camera and the imaging software NIS Elements (BR 3.00, Nikon).

DNA repair assay: For measuring efficiency of NHEJ, an in vitro modified protocol of the EJ5-Isce1 assay was used as described in Bennardo et al., 2008. The pimEJ5GFP reporter (Addgene, Cambridge Mass.) was linearized with I-Sce1 (New England Biolabs, Ipswich, Mass.) at 37° C. overnight, dephosphorylated using Shrimp Alkaline phosphatase (New England Biolabs) for an hour at 37° C. before column purification (Qiagen, Gaithersburg, Md.). For the NHEJ reaction, 500 ng of linearized EJ5-Isce1 was incubated with 5 µg of E-buffer (20 mM Tris-HCl pH 8.0, 20% glycerol, 0.1 mM K (OAc), 0.5 mM EDTA, 1 mM DTT; 2×1 hr) dialyzed N extracts in ligation buffer (10×T4 Ligase Buffer, 2 mM ATP, 50 µM deoxynucleotide triphosphates). After an overnight incubation at 16° C., EJ5 was purified through column purification and subjected to PCR for amplification of GFP genes using the primers P1 (Fwd) 5'-CTGCTAACCATGTTCATGCC-3' (SEQ ID NO:1), p2 (Rev) 5'-AAGTCGTGCTGCTTCATGTG-3' (SEQ ID NO:2), as described by Bennardo et al., 2008. The PCR products were then run on a 2% agarose gel and the product was visualized with the GelStar™ Nucleic Acid Stain (Lonza). Ligated plasmid (PCR product) was calculated relative to total DNA loaded and expressed as relative efficiency of repair (fold changes compared to CRTL). H3 expression was used as loading control for the amount of proteins used in each reaction.

AML xenograft models: Female NSG mice (6-8 weeks old) were used for all in vivo xenograft studies and were housed in a 12-h light/dark cycle with access to food and water ad libitum. Exponentially growing MV4-11-luc cells ($1 \times 10^6$; Dr. Sharyn Baker, St Jude) were injected intravenously into the lateral tail vein of restrained mice. Three days later, cell engraftment was assessed after injection of D-luciferin (150 mg/kg IP) on a Xenogen IVIS-2-Imaging System (Alameda, Calif.). Mice were sorted into 4 treatment groups so that mean intensity of signal was equal. Mice were visually observed daily, weighed 5 days per week and leukemic burden was assessed weekly by non-invasive luciferin imaging. Mice were treated with 0.1 mg/kg BMN673, 0.5 mg/kg 5-AzaC, the combination or vehicle (10% DMAc/6% Solutol/84% PBS for BMN 673 or saline for 5-AzaC). BMN 673 was administered by oral gavage (per os) once daily and 5-AzaC was administered by subcutaneous injection daily, 5 days per week for the duration of the study.

Densitometry and statistical analysis: When applicable, densitometry graphs were done using the Quantity-one software (v.4.6, Bio-Rad) after scanning nonsaturated luminograms and results are represented as fold changes compared to CRTL of three independent experiments ±SEM. All statistical analyses were performed using a Student T-test with * meaning p value <0.05 unless indicated otherwise.

Results

PARP1 interacts with DNMT's in a damage induced, enlarging, protein complex: Others have reported that PARP-1 interacts non-covalently with DNA methyltransferase 1 (Dnmt1; Caiafa et al., 2009), suggesting that epigenetic and DNA repair pathways are linked mechanistically. In the present study, these data have been extrapolated for interaction using a previously reported DNA damage model in which human cancer cells have been exposed to hydrogen peroxide) ($H_2O_2$). Within 30 min of this challenge, an enlarging protein complex was observed, including the three biologically DNMT's, histone deactylases, and polycomb silencing proteins. The damage also induces tightening of complex components to chromatin, especially DNMT1 and localization to sites of DNA damage. In the present work, it was found, in the above model, that a constituent of this complex, including in the enlarging complex size after the DNA damage, is PARP1 (FIG. 14). In these dynamics, PARP1 interacts with DNMT's as evidenced by co-immunoprecipitation assays performed on the sucrose gradient fractions which define the complex size before and after damage (FIG. 14).

DNMTi's and PARPi 's increase trapping at sites of DNA damage: PARPi' s, and especially the new class of potent drugs, such as BMN673, have been shown to not only catalytically inhibit PARP activity but also to trap PARP in chromatin, forming cytotoxic DNA-PARP complexes. Importantly for the present studies, DNMTi's, by their obligatory mechanisms of action, are incorporated into replicating DNA as exogenous nucleotides. Subsequent to this, they covalently bind to the catalytic sites of all three biologically active DNMT's, inhibiting their DNA methylating capacity and triggering degradation especially of the three soluble proteins in the nucleus. However, the drugs also bind DNMT's to their incorporation sites in DNA and, given all of the data in the preceding sections, it was questioned whether PARP1 would be trapped as well—and whether such treatment would enhance capacity of PARPi's to trap PARP1. Using low nM (10 nM and 20 nM DAC) DNMTi administration, and PARPi's ABT888 (500 μM) or BMN673 (10 nM), either sequentially or in combination, to MV411 and MOLM14 AML cells (FIG. 15; Tsai et al., 2012), chromatin extracts from cells X-irradiated (4Gy) to induce DSBs were examined. As expected, by Western blot analyses, PARP1 is increased in chromatin in AML cells treated with 1 nM or 10 nM of potent BMN673, compared with 500 nM or 5 μM of ABT888 (weaker PARPi). However, DAC treatment alone also traps PARP1 in chromatin and combination treatment of this drug with the PARPi's and further increases PARP1 trapping as compared with single drug treatments (FIG. 15). These findings, as pursued in sections below, suggest that combining DNA demethylating agents plus PARPi might have mechanistic ramifications for effects on DNA damage repair and for cancer therapy paradigms.

Figure 16A:
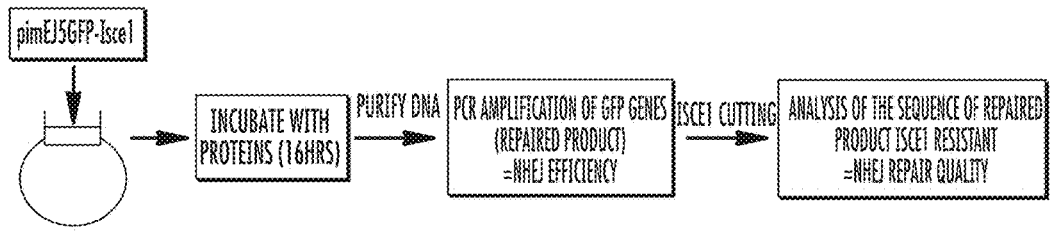
Figure 16B:
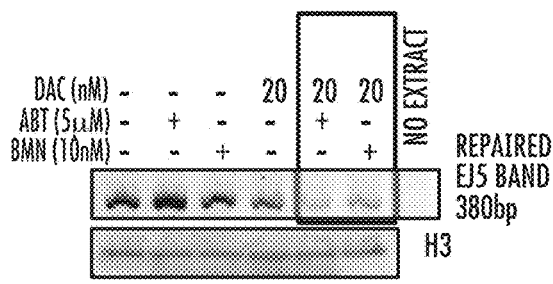
Figure 16C:
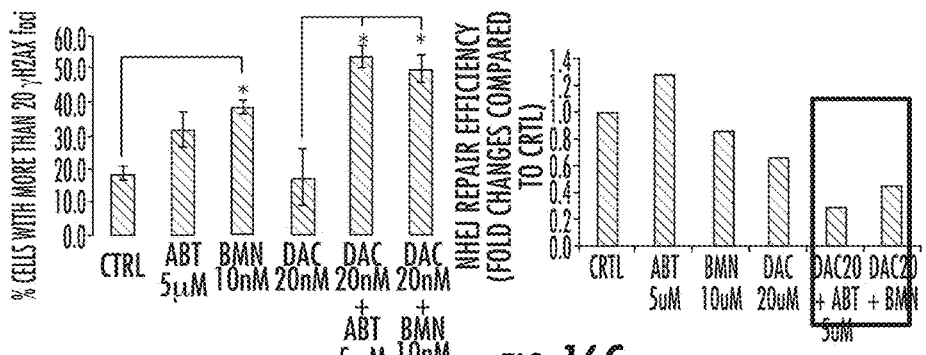

Combining DNMTi's and PARPi's induce decrease in DSB repair: The above data suggests that DNA repair processes involving PARP, including SSB repair, replication-associated repair and ALT NHEJ, should be decreased, via increased trapping of this protein with combinatorial DAC and PARPi's treatment. Given that PARP1 and NHEJ Ku factors compete for binding to DSBs, it was reasoned that PARP trapping may block c-NHEJ repair. Therefore, it was first determined whether treatment with DAC followed by PARPi's altered the efficiency of NHEJ. MV411 was treated daily for 3 days with DAC (20 nM), allowed to recover for 4 days, followed by treatment with either ABT888 (5 μM) or BMN673 (10 nM). NHEJ activity in nuclear extracts, as quantitated by assays with a plasmid-based NHEJ assay using a PIM1EJ5-GFP construct (FIG. 16A; Bennardo et al., 2008), is distinctly decreased with the drug combination, as compared to either drug alone (FIG. 16B). Moreover, BMN673 (10 nM) in combination with DAC (5 nM or 10 nM) show higher percentages of cells with more than 20 γH2AX foci and less NHEJ repair efficiency (FIG. 16C).

Figure 16D:
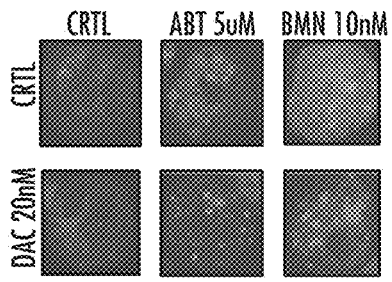
Figure 17A:
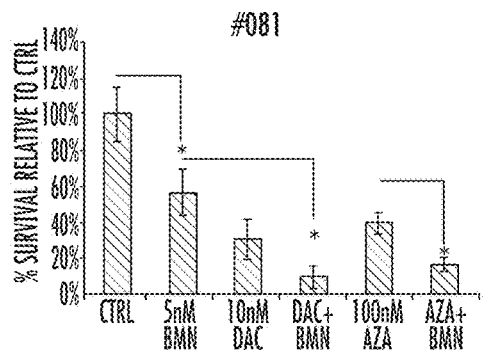
Figure 17B:
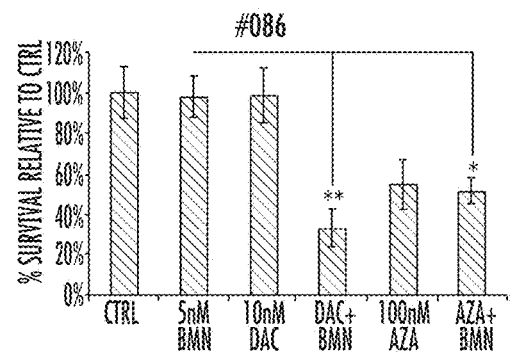
Figure 17C:
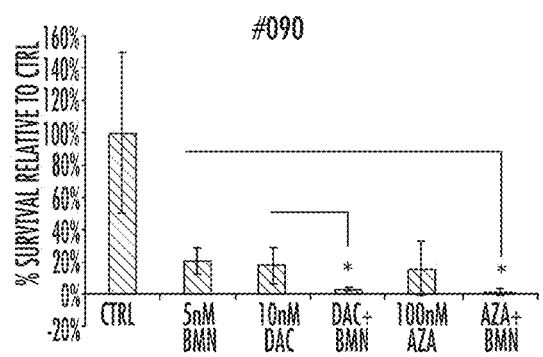
Figure 17D:
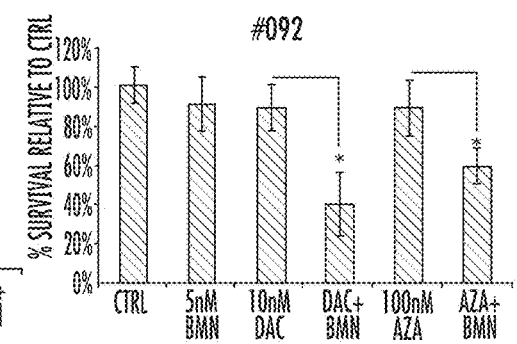

To determine whether the above decreased DSB repair led to an increase in levels of DSBs, γH2AX foci was measured in MV411 following treatment with DAC alone (20 nM), BMN673 (10 nM) or ABT888 (5 μM), alone, and combinations of the drugs. DAC treatment alone gave no increase in foci in these short-term experiments, as previously reported (Tsai et al., 2012). Treatment with BMN673 or ABT888 alone showed an increase in foci, and by comparison, DAC followed by PARPi's showed significantly more γH2AX foci (FIG. 16D).

DNMTi's combined with PARPi's decrease clonogenicity in cultured and primary AML cells: Given that trapping DNA-PARP complexes at sites of DNA damage correlates with cytotoxicity of PARPi's and that DNMTi followed by PARPi decreased clonogenicity in colony survival assays of AML cells in methyl cellulose FIG. 9), it was next determined if the same results were seen in primary samples from AML patients.

The above studies in cultured AML cells were followed with identical treatment protocols for primary samples from 11 AML patients using ABT888 (500 nM) in 7 samples (Patients #9, #15, #16, #18, #29, #30, #34; FIGS. 7A and 21), and additionally, BMN673 (1 nM-10 nM) for 6 samples (Patients #30, #34, #81, #86, #90, #92; FIG. 21). However, most importantly, samples from 7 of 11 patients (Patients #15, #29, #34, #81, #86, #90, #92) showed that pretreatment with DAC further sensitized these cells to ABT888 treatment or BMN673 treatment (1 nM-10 nM). Importantly, as for culture lines MOLM14 and MV411, patient samples #15, #29 and #34 harbor the poor prognosis mutation FLT3-ITD-positive AML (FIG. 21A). Additionally, using DAC (10 nM) or AZAC (100 nM) and BMN 673 (5 nM) administered simultaneously (rather than sequentially), resulted in similar findings of significantly decreased colony survival, compared with single agent treatments (FIGS. 17A-17D). Importantly, normal bone marrow is not affected by the drug concentrations used (FIG. 18).

Together, all of the results in this section, in cell lines and primary cells, show that AML, and in particular FLT3-ITD positive AML cells, treated with DAC/AzaC in combination with PARPi's are significantly sensitive, compared with single drug treatments. This suggests, as tested further below, a potential therapeutic strategy with administration of DNMTi's in combination with PARPi's.

Figure 19:
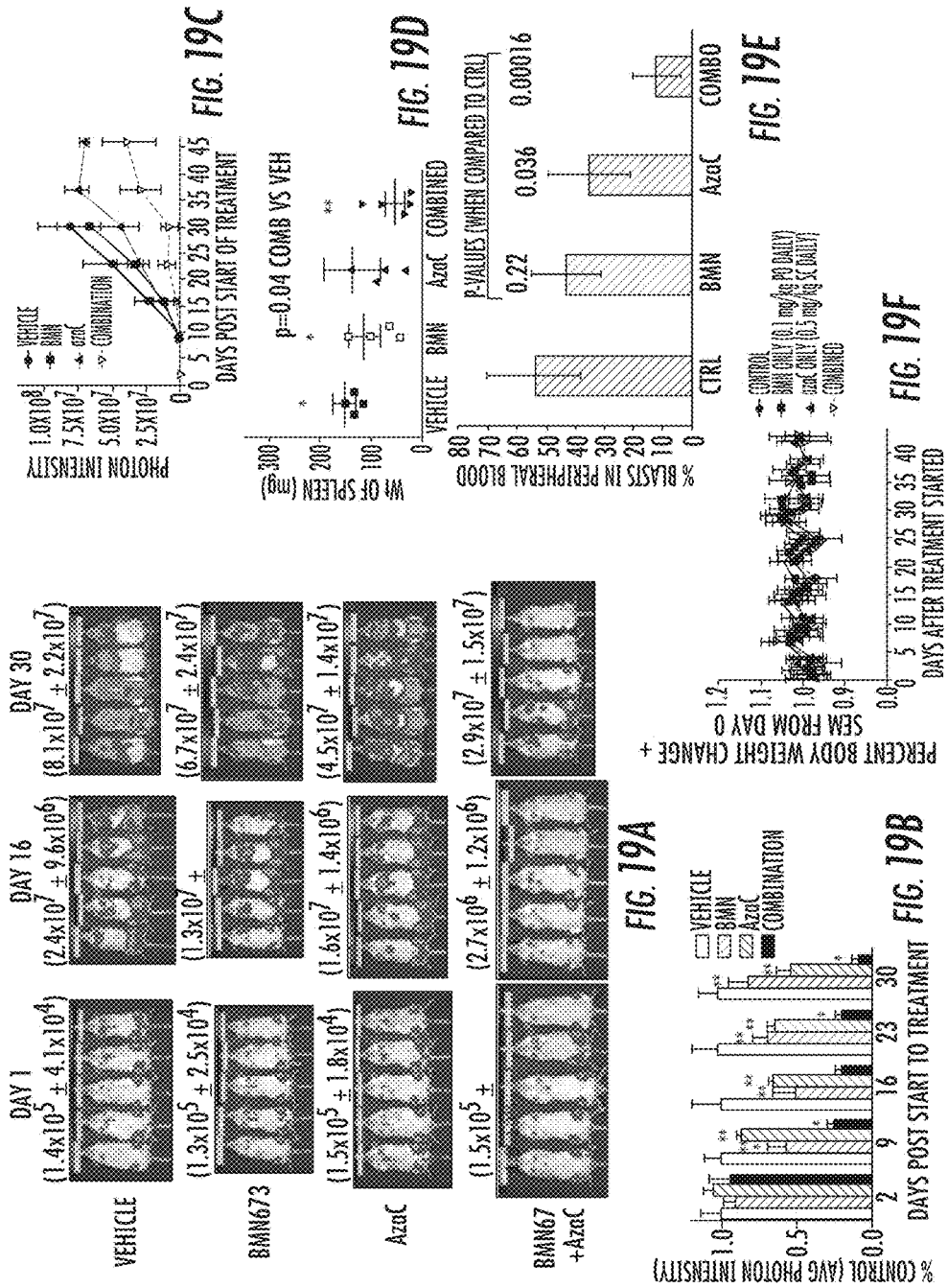

AML xenografts are sensitive to the combination DAC and PARPi's: To determine whether the DNMTi sensitized AML cells were sensitive to PARPi in vivo, mouse xenograft experiments were performed using the FLT3/ITD-positive cell line MV411 stably expressing luciferase (MV411-luc). Male or female NOD.Cg-Prkdcscid Il2rgtm1Wj1/SzJ (NSG) (Stock number: 005557; Jackson Laboratories, Bar Harbor, Me.) animals were given an intravenous injection of $5 \times 10^6$ MV4-11-luc cells. Cell engraftment was assessed after injection of D-luciferin (150 mg/kg i.p.; Perkin Elmer, Waltham, Mass.) on a Xenogen IVIS-200 imaging system (Alameda, Calif.), and mice were randomized to treatment groups based on signal intensity. Treatment groups were vehicle, azacytidine (AzaC) (0.5 mg/kg/day SC 5 days/week), BMN (1 mg/kg PO 5 days/week) and the two drugs combined. Leukemic burden was monitored weekly by noninvasive luciferase imaging, and mice were observed daily and euthanized humanely upon signs of terminal illness (hind limb paralysis, inability to eat/drink, moribund lethargy). MV4-11-luc cells were engrafted in the bone marrow by day 7 in males and day 9 in females after cell injection. At the time of terminal illness, >90% leukemic cell infiltration in the bone marrow was observed. As measured by photon intensity, results show that the combination of BMN673 and AzaC result in a significant ($p<0.01$) decrease in tumor burden up to day 30 following treatment, compared with either drug alone (FIGS. 19A,B). While leukemia burden increased in all groups after day 30 post treatment (FIG. 19C), by the end of the experiment, leukemia burden, spleen weight and blasts in the peripheral blood showed significantly decreased disease with the treatment combination, compared with either drug treatment alone (FIGS. 19D,E). All treatments were well tolerated (FIG. 19F). Results also showed that the combination of BMN673 and AzaC led to higher survival as compared to BMN673 alone (FIG. 20).

Discussion

The development of poly (ADP-ribose) polymerase (PARP) inhibitors represents one of the most exciting recent developments in cancer therapy. While substantial efficacy has been shown with clinically available PARP inhibitors, to date, in treatment of hereditary deletions of BRCA1/2 in breast and ovarian cancers, the high promise of these drugs has not yet been realized for non-BRCA1/2 defective cancers. The present studies show for the first time in AML that DNMTi in combination with potent PARPi's BMN673 acts through increased trapping of DNA-PARP complexes on chromatin. These complexes result in decreased DSB repair and increased cytotoxic DSBs in vitro and in vivo. This novel treatment strategy is particularly important in the FLT/3/ITD-positive subgroup of AML that confers a poor prognosis and for which little therapeutic options are available.

Using established plasmid based assays that measure NHEJ, it was shown for the first time that treatment with PARP inhibitors decreases NHEJ efficiency, but that DAC pre-treatment decreases this repair activity even further. Interestingly, recent studies have suggested that DAC could affect NHEJ repair efficiency (Moscariello and Iliakis, 2013). Notably, this effect could explain why pretreatment with DAC followed by PARPi's or the two drugs in combination are a potent inducer of cytotoxicity, as these two drugs collaborate in reducing/shutting down AML cells capacity to repair DSBs. A high activity and potential cellular "dependence" on this pathway in leukemic and breast cancer cells was previously demonstrated, which are characterized by dependence on high PARP-1 expression levels and activity.

These studies demonstrate a novel and compelling therapeutic paradigm of DNMTi in combination PARP inhibitors, such as BMN673, for AML. These pre-clinical studies will allow rapid advancement of this novel therapeutic strategy to a clinical trial, to test the efficacy of epigenetic therapy prior to PARP inhibitor therapy for MDS and AML. These studies will lay the groundwork for similar combinatorial studies in other cancers, such as receptor negative breast cancer. In addition, these studies may yield greater insights into the mechanisms by which DNA repair and epigenetic pathways interact, suggesting other therapeutic targets.

Example 3

Synergy of DNA Demethylating Agents and PARP Inhibitors

Combination Index plots using CompuSyn software (ComboSyn, Inc.) were generated for MOLM14 cells treated daily for 7 days with the PARP inhibitor BMN673 (0.5, 1, 2, and 4 nM) and either DMNT1 inhibitors decitabine (5, 10, 20, 40 nM) or 5-Azacytidine (50, 100, 200, 400 nM) (FIG. 22). The MTS assay (Promega, Madison, Wis.), a colorimetric method for determining the number of viable cells and therefore cytotoxicity, was used to measure cell viability and cytotoxicity following various drug treatments and these values were used to calculate synergy. The x-axis represents the fraction of cells affected (Fa) and the Y-axis the combination index (CI). Each point represents one combination treatment (e.g., 0.5 nM BMN and 50 nM AZA, etc). The horizontal line represents the value CI=1, where a particular drug combination is additive. Any points below the horizontal line (CI<1) represent synergistic combinations, and CI values above the line (CI>1) represent antagonistic combinations. All combinations (except 1 nM BMN/10 nM DAC and 1 nM BMN/100 nM AZA) exhibit synergism.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Agger K, Christensen J, Cloos P A, Helin K. The emerging functions of histone demethylases. Curr Opin Genet Dev. 2008; 18(2):159-168.

Audebert, M., Salles, B., and Calsou, P. (2004). Involvement of poly(ADP-ribose) polymerase-1 and XRCC1/DNA ligase III in an alternative route for DNA double-strand breaks rejoining. J Biol Chem 279, 55117-55126.

Audebert, M., Salles, B., Weinfeld, M., and Calsou, P. (2006). Involvement of polynucleotide kinase in a poly (ADP-ribose) polymerase-1-dependent DNA double-strand breaks rejoining pathway. J Mol Biol 356, 257-265.

Baylin S B, Jones P A. A decade of exploring the cancer epigenome—biological and translational implications. Nat Rev Cancer. 2011; 11(10):726-734.

Beneke S. Regulation of chromatin structure by poly (ADP-ribosyl)ation. Front Genet. 2012; 3169.

Bennardo, N., Cheng, A., Huang, N., and Stark, J. M. (2008). Alternative-NHEJ is a mechanistically distinct pathway of mammalian chromosome break repair. PLoS Genet 4, e1000110.

Blum, W., Klisovic, R. B., Hackanson, B., Liu, Z., Liu, S., Devine, H., Vukosavljevic, T., Huynh, L., Lozanski, G., Kefauver, C., et al. (2007). Phase I study of decitabine alone or in combination with valproic acid in acute myeloid leukemia. J Clin Oncol 25, 3884-3891.

Bryant, H. E., Schultz, N., Thomas, H. D., Parker, K. M., Flower, D., Lopez, E., Kyle, S., Meuth, M., Curtin, N. J., and Helleday, T. (2005). Specific killing of BRCA2-deficient tumours with inhibitors of poly(ADP-ribose) polymerase. Nature 434, 913-917.

Bullinger, L., Dohner, K., Kranz, R., Stirner, C., Frohling, S., Scholl, C., Kim, Y. H., Schlenk, R. F., Tibshirani, R., Dohner, H., and Pollack, J. R. (2008). An FLT3 gene-expression signature predicts clinical outcome in normal karyotype AML. Blood 111, 4490-4495.

Caiafa, P., Guastafierro, T., and Zampieri, M. (2009). Epigenetics: poly(ADP-ribosyl)ation of PARP-1 regulates genomic methylation patterns. FASEB J 23, 672-678.

Cashen, A. F., Shah, A. K., Todt, L., Fisher, N., and DiPersio, J. (2008). Pharmacokinetics of decitabine administered as a 3-h infusion to patients with acute myeloid leukemia (AML) or myelodysplastic syndrome (MDS). Cancer Chemother Pharmacol 61, 759-766.

Durkacz, B. W., Omidiji, a., Gray, D. A., and Shall, S. (1980). (ADP-ribose)n participates in DNA excision repair. Nature 283, 593-596.

Fan J, Robert C, Jang Y Y, et al. Human induced pluripotent cells resemble embryonic stem cells demonstrating enhanced levels of DNA repair and efficacy of nonhomologous end-joining. Mutat Res. 2011; 713(1-2):8-17.

Farmer, H., McCabe, N., Lord, C. J., Tutt, A. N., Johnson, D. A., Richardson, T. B., Santarosa, M., Dillon, K. J., Hickson, I., Knights, C., et al. (2005). Targeting the DNA repair defect in BRCA mutant cells as a therapeutic strategy. Nature 434, 917-921.

Fattah, F., Lee, E. H., Weisensel, N., Wang, Y., Lichter, N., and Hendrickson, E. A. (2010). Ku regulates the non-homologous end joining pathway choice of DNA double-strand break repair in human somatic cells. PLoS Genet 6, e1000855.

Gaymes T J, Mohamedali A M, Patterson M, et al., (2013). Microsatellite instability induced mutations in DNA repair genes CtIP and MRE11 confer hypersensitivity to poly (ADP-ribose) polymerase inhibitors in myeloid malignancies. Haematologica, 98(9):1397-406.

Gaymes, T. J., North, P. S., Brady, N., Hickson, I. D., Mufti, G. J., and Rassool, F. V. (2002). Increased error-prone non homologous DNA end-joining—a proposed mechanism of chromosomal instability in Bloom's syndrome. Oncogene 21, 2525-2533.

Gaymes T J, Shall S, MacPherson L J, et al., (2009) Inhibitors of poly ADP-ribose polymerase (PARP) induce apoptosis of myeloid leukemic cells: potential for therapy of myeloid leukemia and myelodysplastic syndromes. Haematologica. 94(5):638-46.

Guha M. PARP inhibitors stumble in breast cancer. Nat Biotechnol. 2011; 29(5):373-374.

Haince J F, Kozlov S, Dawson V L, et al. Ataxia telangiectasia mutated (ATM) signaling network is modulated by a novel poly(ADP-ribose)-dependent pathway in the early response to DNA-damaging agents. J Biol Chem. 2007; 282(22):16441-16453.

Hassa, P. O., and Hottiger, M. O. (2008). The diverse biological roles of mammalian PARPS, a small but powerful family of poly-ADP-ribose polymerases. Front Biosci 13, 3046-3082.

Helleday, T. (2011). The underlying mechanism for the PARP and BRCA synthetic lethality: clearing up the misunderstandings. Molecular oncology 5, 387-393.

Helleday T, Bryant H E, Schultz N. Poly(ADP-ribose) polymerase (PARP-1) in homologous recombination and as a target for cancer therapy. *Cell Cycle*. 2005; 4(9):1176-1178.

Helleday, T., Petermann, E., Lundin, C., Hodgson, B., and Sharma, R. A. (2008). DNA repair pathways as targets for cancer therapy. Nat Rev Cancer 8, 193-204.

Isakoff, S. J. (2010). Triple-negative breast cancer: role of specific chemotherapy agents. Cancer J 16, 53-61.

Issa, J. P., Garcia-Manero, G., Giles, F. J., Mannari, R., Thomas, D., Faderl, S., Bayar, E., Lyons, J., Rosenfeld, C. S., Cortes, J., and Kantarjian, H. M. (2004). Phase 1 study of low-dose prolonged exposure schedules of the hypomethylating agent 5-aza-2'-deoxycytidine (decitabine) in hematopoietic malignancies. Blood 103, 1635-1640.

Jones, P. A. (2002). DNA methylation and cancer. Oncogene 21, 5358-5360.

Jones, P. A., and Taylor, S. M. (1980). Cellular differentiation, cytidine analogs and DNA methylation. Cell 20, 85-93.

Juergens R A, Wrangle J, Vendetti F P, et al. Combination epigenetic therapy has efficacy in patients with refractory advanced non-small cell lung cancer. Cancer Discov. 2011; 1(7):598-607.

Kantarjian, H., Issa, J. P., Rosenfeld, C. S., Bennett, J. M., Albitar, M., DiPersio, J., Klimek, V., Slack, J., de Castro, C., Ravandi, F., et al. (2006). Decitabine improves patient outcomes in myelodysplastic syndromes: results of a phase III randomized study. Cancer 106, 1794-1803.

Kashima L, Idogawa M, Mito H, et al. CHFR protein regulates mitotic checkpoint by targeting PARP-1 protein for ubiquitination and degradation. J Biol Chem. 2012; 287(16): 12975-12984.

Khanna, K. K., and Jackson, S. P. (2001). DNA double-strand breaks: signaling, repair and the cancer connection. Nat Genet 27, 247-254.

Khanna K K, Lavin M F, Jackson S P, Mulhem T D. ATM, a central controller of cellular responses to DNA damage. Cell Death Differ. 2001; 8(11):1052-1065.

Kouzarides T. Chromatin modifications and their function. Cell. 2007; 128(4):693-705.

McCabe N. Turner N C, Lord C J, et al. Deficiency in the repair of DNA damage by homologous recombination and sensitivity to poly (ADP-ribose) polymerase inhibition. Cancer Res. 2006; 66(16):8109-8115.

Moscariello, M., and Iliakis, G. (2013). Effects of chromatin decondensation on alternative NHEJ. DNA Repair (Amst) 12, 972-981.

Murai, J., Huang, S. Y., Das, B. B., Renaud, A., Zhang, Y., Doroshow, J. H., Ji, J., Takeda, S., and Pommier, Y. (2012). Trapping of PARP1 and PARP2 by Clinical PARP Inhibitors. Cancer Res 72, 5588-5599.

Murai, J., Huang, S. Y., Renaud, A., Zhang, Y., Ji, J., Takeda, S., Morris, J., Teicher, B., Doroshow, J. H., and Pommier, Y. (2014). Stereospecific PARP trapping by BMN 673 and comparison with olaparib and rucaparib. Mol Cancer Ther 13, 433-443.

Noel, G., Godon, C., Fernet, M., Giocanti, N., Megnin-Chanet, F., and Favaudon, V. (2006). Radiosensitization by the poly(ADP-ribose) polymerase inhibitor 4-amino-1,8-naphthalimide is specific of the S phase of the cell cycle and involves arrest of DNA synthesis. Mol Cancer Ther 5, 564-574.

O'Hagan, H. M., Wang, W., Sen, S., Destefano Shields, C., Lee, S. S., Zhang, Y. W., Clements, E. G., Cai, Y., Van Neste, L., Easwaran, H., et al. (2011). Oxidative damage targets complexes containing DNA methyltransferases, SIRT1, and polycomb members to promoter CpG Islands. Cancer Cell 20, 606-619.

Rassool, F. V., and Tomkinson, A. E. (2010). Targeting abnormal DNA double strand break repair in cancer. Cell Mol Life Sci 67, 3699-3710.

Rauth S, Song K Y, Ayares D, Wallace L, Moore P D, Kucherlapati R, Transfection and homologous recombination involving single-stranded DNA substrates in mammalian cells and nuclear extracts. Proc Natl Acad Sci USA. 1986; 83(15):5587-5591.

Robert C, Rassool F V. HDAC inhibitors: roles of DNA damage and repair. Adv Cancer Res. 2012; 11687-129.

Rouleau, M., Patel, A., Hendzel, M. J., Kaufmann, S. H., and Poirier, G. G. (2010). PARP inhibition: PARP1 and beyond. Nat Rev Cancer 10, 293-301.

Saleh-Gohari, N., Bryant, H. E., Schultz, N., Parker, K. M., Cassel, T. N., and Helleday, T. (2005). Spontaneous homologous recombination is induced by collapsed replication forks that are caused by endogenous DNA single-strand breaks. Mol Cell Biol 25, 7158-7169.

Sallmyr, A., Fan, J., Datta, K., Kim, K. T., Grosu, D., Shapiro, P., Small, D., and Rassool, F. (2008a). Internal tandem duplication of FLT3 (FLT3/ITD) induces increased ROS production, DNA damage, and misrepair: implications for poor prognosis in AML. Blood 111, 3173-3182.

Sallmyr, A., Tomkinson, A. E., and Rassool, F. V. (2008b). Up-regulation of WRN and DNA ligase IIIalpha in chronic myeloid leukemia: consequences for the repair of DNA double-strand breaks. Blood 112, 1413-1423.

Schiltz R L, Mizzen C A, Vassilev A, Cook R G, Allis C D, Nakatani Y. Overlapping but distinct patterns of histone acetylation by the human coactivators p300 and PCAF within nucleosomal substrates. J Biol Chem. 1999; 274(3): 1189-1192.

Shen, Y., Rehman, F. L., Feng, Y., Boshuizen, J., Bajrami, I., Elliott, R., Wang, B., Lord, C. J., Post, L. E., and Ashworth, A. (2013). BMN 673, a Novel and Highly Potent PARP1/2 Inhibitor for the Treatment of Human Cancers with DNA Repair Deficiency. Clin Cancer Res 19, 5003-5015.

Tobin L A, Robert C, Nagaria P, Chumsri S, Twaddell W, Ioffe O B, Greco G E, Brodie A H, Tomkinson A E, Rassool F V. Targeting abnormal DNA repair in therapy-resistant breast cancers. Mol Cancer Res. 2012; 10(1):96-107.

Tobin, L. A., Robert, C., Rapoport, A. P., Gojo, I., Baer, M. R., Tomkinson, A. E., and Rassool, F. V. (2013). Targeting abnormal DNA double-strand break repair in tyrosine kinase inhibitor-resistant chronic myeloid leukemias. Oncogene 32, 1784-1793.

Tsai, H. C., Li, H., Van Neste, L., Cai, Y., Robert, C., Rassool, F. V., Shin, J. J., Harbom, K. M., Beaty, R., Pappou, E., et al. (2012). Transient low doses of DNA-demethylating agents exert durable antitumor effects on hematological and epithelial tumor cells. Cancer Cell 21, 430-446.

Venkitaraman A R. Cancer susceptibility and the functions of BRCA1 and BRCA2. Cell. 2002; 108(2):171-182.

Zhang, Y. W., Regairaz, M., Seiler, J. A., Agama, K. K., Doroshow, J. H., and Pommier, Y. (2011). Poly(ADP-ribose) polymerase and XPF-ERCC1 participate in distinct pathways for the repair of topoisomerase I-induced DNA damage in mammalian cells. Nucleic Acids Res 39, 3607-3620.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating ovarian cancer, the method comprising administering to a subject in need of treatment thereof an effective amount of a DNA demethylating agent and an effective amount of a poly ADP ribose polymerase (PARP) inhibitor, wherein the DNA demethylating agent is a DNA methyltransferase inhibitor (DNMTi).

2. The method of claim 1, wherein the DNMTi is selected from the group consisting of 5-azacitidine, decitabine, guadecitabine (SGI-110) and disulfiram.

3. The method of claim 1, wherein the PARP inhibitor is selected from the group consisting of Veliparib, talazoparib (BMN-673), 4-iodo-3-nitrobenzamide, Olaparib, Rucaparib, and 11-methoxy-2-((4-methylpiperazin-1-yl)methyl)-4,5,6,7-tetrahydro-1H-cyclopenta[a]pyrrolo[3,4-c]carbazole-1,3(2H)-dione (CEP 9722).

4. The method of claim 1, wherein the effective amount of the DNMTi is less than about 100 mg/m$^2$.

5. The method of claim 1, wherein the effective amount of the DNMTi is from about 20 mg/m$^2$ to about 75 mg/m$^2$.

6. The method of claim 1, wherein the effective amount of the PARP inhibitor is less than about 1 mg/m$^2$.

7. The method of claim 1, wherein the effective amount of the PARP inhibitor is less than about 500 mg/m$^2$.

8. The method of claim 1, wherein the effective amount of the PARP inhibitor is from about 1 to about 500 mg/m$^2$.

9. The method of claim 1, wherein the DNMTi and the PARP inhibitor are each given in a once daily dose.

10. The method of claim 1, wherein the subject is human.

11. The method of claim 1, wherein the treating of the cancer includes reducing the double-stranded DNA repair mechanism in one or more of the cancer cells in the subject.

12. The method of claim 1, wherein the treating of the cancer includes increasing the number of cytotoxic DNA-PARP complexes in the chromatin in one or more of the cancer cells in the subject.

13. The method of claim 1, wherein the DNMTi is administered prior to the PARP inhibitor.

14. The method of claim 1, wherein the DNMTi is administered simultaneously with the PARP inhibitor.

15. The method of claim 1, wherein the effect of the DNMTi and the PARP inhibitor is synergistic.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
ctgctaacca tgttcatgcc                                          20

<210> SEQ ID NO 2
<211> LENGTH: 20
<212> TYPE: DNA

```
<213> ORGANISM: Artificial Sequence
<220> FEATURE:
<223> OTHER INFORMATION: PCR primer

<400> SEQUENCE: 2
aagtcgtgct gcttcatgtg                                                    20
```